US005646035A

United States Patent [19]
Coon et al.

[11] Patent Number: 5,646,035
[45] Date of Patent: Jul. 8, 1997

[54] METHOD FOR PREPARING AN EXPANDED CULTURE AND CLONAL STRAINS OF PANCREATIC, THYROID OR PARATHYROID CELLS

[75] Inventors: Hayden G. Coon, Gaithersburg, Md.; Francesco Saverio Ambesi-Impiombato, Tricesimo; Francesco Curcio, Pagnacco, both of Italy

[73] Assignee: Human Cell Cultures, Inc., Gaithersburg, Md.

[21] Appl. No.: 480,149

[22] Filed: Jun. 7, 1995

Related U.S. Application Data

[63] Continuation of Ser. No. 83,772, Jun. 30, 1993, abandoned, which is a continuation-in-part of Ser. No. 44,010, Apr. 8, 1993, abandoned.
[51] Int. Cl.$^6$ .................... C12N 5/06; C12N 5/08; C12N 5/00
[52] U.S. Cl. .................... 435/378; 435/383; 435/397
[58] Field of Search .................... 435/240.2, 240.21, 435/240.3, 240.31

[56] References Cited

U.S. PATENT DOCUMENTS

| | | | |
|---|---|---|---|
| 4,673,649 | 6/1987 | Boyce et al. | 435/240 |
| 4,940,666 | 7/1990 | Boyce et al. | 435/240.2 |
| 5,143,666 | 9/1992 | Ham et al. | 435/240.2 |
| 5,153,132 | 10/1992 | Goodwin et al. | 435/240.24 |
| 5,155,034 | 10/1992 | Wolf et al. | 435/240.24 |
| 5,308,764 | 5/1994 | Goodwin et al. | 435/240.24 |
| 5,330,908 | 7/1994 | Spaulding | 435/240.24 |
| 5,496,722 | 3/1996 | Goodwin et al. | 435/240.23 |
| 5,523,228 | 6/1996 | Ingram et al. | 435/240.25 |
| 5,545,423 | 8/1996 | Soon-Shiong et al. | 424/484 |

FOREIGN PATENT DOCUMENTS

| | | |
|---|---|---|
| 9114004 | 9/1991 | WIPO . |
| WO92/21979 | 12/1992 | WIPO . |
| 9300441 | 1/1993 | WIPO . |
| WO93/24112 | 12/1993 | WIPO . |

OTHER PUBLICATIONS

Freshney, *Culture of Animal Cells: A Manual of Basic Technique*, pp. 119–143 (1983).
Ambesi–Impiombato et al, Proc. Natl. Acad. Sci USA, 77(6) (Jun. 1980) pp. 3455–3459.
Nielsen, Acta Endocrinol. Suppl (Copenh) vol. 266 (1985) pp. 1–39.
Hulinsky, Transplant Proc. (US), 24(6) (Dec. 1992) p. 2819.
Hu et al., Chinese Medical Journal, 105 (9): 721–725 (1992).
Cooney et al, Diabetologia, V 35, S1, p. A124 (Aug. 1992).
Hellerstrom et al., Diabetes, vol 40 (Suppl. 2), pp. 89–93 (1991).
Tsubouchi et al, Anat. Rec, vol 218, No. 2, pp. 111–115 (1987).
Dunger et al, Horm. Metab. Res., 23: 201–204 (1991).
Brelje et al., "Role of Prolactin Versus Growth Hormone on Islet B–Cell Proliferation in Vitro: Implications for Pregnancy," *Endocrinology*, 128:45–57 (1991).
Clark et al., "Islet Cell Culture in Defined Serum–Free Medium," *Endocrinology*, 126:1895–1903 (1990).
Coon et al., "Cell Cultures of Neuroblasts from Rat Olfactory Epithelium that Show Odorant Responses," *Proc. Natl. Acad. Sci. U.S.A.*, 86:1703–1707 (1989).
Feutren et al., "Cyclosporin Increases the Rate and Length of Remissions in Insulin–Dependent Diabetes of Recent Onset," *Lancet*, 11:119–123 (1986).
Jaworski et al., "Cyclosporin Prophylaxis Induces Long–Term Prevension of Diabetes, and Inhibits Lymphocytic Infiltration in Multiple Target Tissues in the High–Risk BB Rat," *Diabetes Res.*, 3:1–6 (1986).
Mori et al., "Preventive Effects of Cyclosporin on Diabetes in NOD Mice," *Diabetologia*, 29:244–247 (1986).
R. Paul Robertson, M.D., "Pancreatic and Islet Transplantation for Diabetes —Cures or Curiosities?," *New England J. Med.*, 327:1861–1868 (1992).
Beattie et al., "Functional Impact of Attachment and Purification in the Short Term Culture of Human Pancreatic Islets," *Endocrinology*, 73:93–98 (1991).
Berry et al., "Bone–Marrow–Derived Chondrogenisis In Vitro," *Journal of Cell Science*, 101:333–342 (1992).
Braun et al., "Long–Term Treatment With Glucocorticoids Increases Synthesis and Stability of Juntional Acetylcholine Receptors on Innervated Cultured Human Muscle," *J. Neurochem.*, 60:1929–1935 (1993).
Brayden et al., "A Novel Method for Culturing Sweat Gland Epithelia: Comparison of Normal and Cystic Fibrosis Tissues," *Br. J. Clin. Pharmac.*, 29:235–238 (1990).
Carlson et al., "Asynaptic Expression of the Adult Nicotinic Acetylcholine Receptor in Long–Term Cultures of Mammalian Myotubes," *Developmental Brain Research*, 72:245–252 (1993).

(List continued on next page.)

*Primary Examiner*—John W. Rollins
*Assistant Examiner*—Kristin Larson
*Attorney, Agent, or Firm*—Leydig, Voit & Mayer, Ltd.

[57] ABSTRACT

The present invention provides a method for producing an expanded non-transformed cell culture comprising the steps of: (1) preparing partially purified, minced tissue; (2) concentrating the resulting cells and tissue pieces; (3) resuspending the concentrated tissue cells and pieces in a culture medium capable of supporting sustained cell division that is contained in a culture vessel; (4) incubating the cells; and (5) passaging the cells periodically. The present invention further provides clonal strains of cells derived from the abovementioned cell culture, medium and conditioned medium designed for the culturing of such cells, including pancreatic, thyroid, parathyroid, and parotid cells, and the use of cultured pancreatic cells to form pancreatic pseudotissues composed of matrix-embedded aggregated (pseudoislets) or individual cells, to treat blood sugar disorders in mammals, and to test for cytotoxicity and autoimmune activities with reference to pancreatic endocrine cells.

16 Claims, 11 Drawing Sheets

OTHER PUBLICATIONS

Curcio et al., "Decreased Cultured Endothelial Cell Proliferation in High Glucose Medium is Reversed by Antioxidants: New Insights On the Pathophysiolosical Mechanisms of Diabetic Vascular Complications," *In Vitro Cell. Dev. Biol.*, 28A:787–790 (1992).

de Jong et al., "Serial Culturing of Human Bronchal Epithelial Cells Derived From Biopsies," *In Vitro Cell. Dev. Biol.*, 29A:379–387 (1993).

Dunger et al. "The Effect of Human Amniotic Fluid in Supporting Long-Term Survival of Pancreatic Islets in Tissue Culture," *Horm. Metab. Res.*, 23:201–204 (1991).

Ebert et al., "Establishment and Characterization of Human Renal Cancer and Normal Kdiney Cell Lines," *Cancer Research*, 50:5531–5536 (1990).

Ethier et al., "Differential Isolation of Normal Luminal Mammary Epithelial Cells and Breast Cancer Cells from Primary and Metastatic Sites Using Selective Media," *Cancer Research*, 53:627–635 (1993).

Guy et al., "Isolation and Maintenance of the Human Pilosebaceous Duct" 13–cis Retinoic Acid Acts Directly on the Duct In Vitro, *British Journal of Dematology*, 128:242–248 (1993).

Jaffe et al., "Culture of Human Endothelial Cells Derived From Umbilical Veins," *The Journal of Clinical Investigation*, 52:2745–2756 (1973).

Jensen et al., "Tissue Culture of Human Epidermal Keratinocytes: A Differentiating Model System for Gene Testing and Somatic Gene Therapy," *Journal of Cell Science*, 100:255–259 (1991).

Lewis et al., "Use of Microgravity Bioreactors for Development of an In Vitro Rat Salivary Gland Cell Culture Model," *Journal of Cellular Biochemistry*, 51:265–273 (1993).

Marchetti et al., "In Vitro Function and Xenotransplantation of Long–Term (3 Weeks) Cultured Porcine Islets of Langerhans," *Transplantation Proceedings*, 24:637 (1992).

Oda et al., "Human Oral Epithelial Cell Culture I. Improved Conditions for Reproducible Culture in Serum–Free Medium," *In Vitro Cell. Dev. Biol.*, 26:589–595 (1990).

Pixley, "Purified Cultures of Keratin–Positive Olfactory Epithelial Cells: Identification of a Subset as Neuronal Supporting (Sustentacular) Cells," *Journal of Neuroscience Research*, 31:693–707 (1992).

Pronk et al., "A Cobblestone Cell isolated From the Human Omentum: The Mesothelial Cell; Isolation, Identification, and Growth Characteristics," *In Vitro Cell. Dev. Biol.*, 29A:127–134 (1993).

Ray et al., "Proliferation, Differentiation, and Long–Term Culture of Primary Hippocampal Neurons," *Proc. Natl. Acad. Sci.*, 90:3602–3606 (1993).

Romagnoli et al., "Treatment of Posterior Hypospadias by the Autologous Graft of Cultured Urethral Epithelium," *The New England Journal of Medicine*, 323:527–530 (1990).

Rutkowski et al., "Selective Culture of Mitoically Active Human Schwann Cells from Adult Sural Nerves," *Annals of Neurology*, 31:580–586 (1992).

Solursh, "Formation of Cartilage Tissue In Vitro," *Journal of Cellular Biochemistry*, 45:258–260 (1991).

Speirs et al., "An Overview of Culture and Isolation Methods Suitable for In Vitro Studies on Pulmonary Neuroendocrine Cells," *The Anatomical Record*, 236:35–40 (1993).

Vacanti et al., "Tissue–Engineered Growth of Bone And Cartilage," *Transplantation Proceedings*, 25:1019–1021 (1993).

Volpi et al., "An Efficient Method for Culturing Human Breast Epithelium: Analysis of Results," *Tumori*, 77:460–464 (1991).

Wilson et al., "Epithelial–Specific Gene Expression During Differentiation of Stratified Primary Human Keratinocyte Cultures," *Cell Growth & Differentiation*, 3:471–483 (1992).

Wineman et al., "Maintenance of High Levels of Pluripotent Hematopoietic Stem Cells In Vitro: Effect of Stromal Cells and c–kit," *Blood* 81:365–372 (1993).

METHOD FOR PREPARING AN EXPANDED CULTURE AND CLONAL STRAINS OF PANCREATIC, THYROID OR PARATHYROID CELLS

This is a continuation of application Ser. No. 08/083,772 filed on Jun. 30, 1993, now abandoned, which is a continuation in part of Ser. No. 08/044,010 filed on Apr. 8, 1993, now abandoned.

FIELD OF THE INVENTION

This invention relates to a method and medium for the culturing of differentiated mammalian cells.

BACKGROUND OF THE INVENTION

Many kinds of cells can be grown in culture, provided that suitable nutrients and other conditions for growth are supplied. Thus, since 1907 when Harrison noticed that nerve tissue explanted from frog embryos into dishes under clotted frog lymph developed axonal processes, scientists have made copious use of cultured tissues and cells from a variety of sources. Such cultures have been used to study genetic, physiological, and other phenomena, as well as to manufacture certain macromolecules using various fermentation techniques known in the art. In studies of mammalian cell biology, cell cultures derived from lymph nodes, muscle, connective tissue, kidney, dermis and other tissue sources have been used. Generally speaking, the tissue sources that have been most susceptible to the preparation of cell cultures for studies are derivatives of the ancestor mesodermal cells of early development. Tissues that are the progeny of the ancestor endodermal and ectodermal cells have only in recent years become amenable to cell culture, of a limited sort only. The cell types derived from the endoderm and ectoderm of early development include epidermis, hair, nails, brain, nervous system, inner lining of the digestive tract, various glands, and others. Essentially, long-term cultures of normal differentiated glandular and epithelial cells, particularly those from humans, are still not available.

In the instance of the mammalian pancreas, until the present invention, no scientist has had the opportunity of studying, and no physician has had the prospect of using for treatment, a cell culture of pancreatic endocrine cells that exhibited sustained cell division and the glandular properties typical of the pancreas.

Similar to neurons, the endocrine cells of the mammalian pancreas have been considered to be post-mitotic, i.e., terminal, essentially non-dividing cells. Recent work has shown that the cells of the mammalian pancreas (including those of humans) are capable of survival in culture, but are not capable of sustained cell division. Hence, a primary culture of the tissue cells can succeed, but due to a lack of sufficient cell divisions of the cultured cells, passaging of the primary culture to form serial cultures has not been possible. Although occasional cells in a metaphase stage, uptake of tritiated thymidine, and other evidence of cell division have been seen in these cultures (Clark et al., *Endocrinology*, 126:1895 (1990); Breljie et al., *Endocrinology*, 128:45 (1991)), the overall rate of cell division has been considered to be below the replacement rate (that is, more, or as many, cells die as are produced). Therefore, pancreatic endocrine cell cultures prior to the present invention were not expanded.

The inability to study pancreatic endocrine cells in culture has impeded the ability of medical science to progress in the area of pancreatic disorders. Such disorders include diabetes mellitus, a disease that impairs or destroys the ability of the beta cells of the islets of Langerhans (structures within the pancreas) to produce sufficient quantities of the hormone insulin, a hormone that serves to prevent accumulation of sugar in the bloodstream. Type I diabetes mellitus (insulin dependent, or juvenile-onset diabetes) typically requires full hormone replacement therapy. In a second (and more common) form of the disease, type II diabetes (sometimes referred to as late onset, or senile diabetes), treatment often does not require insulin injections because a patient suffering with Type II diabetes may be able to control his/her blood sugar levels by carefully controlling food intake. However, as many as 30% of these patients also have reduced beta cell function and therefore are candidates for hormone replacement therapy as well. Diabetes is not confined to humans, but has been noted in other mammals as well, such as dogs and horses.

The etiology of the diabetic disease condition is not fully understood. However, it has been noted that autoimmunity antibodies (antibodies that "mistakenly" attack bodily structures) and/or certain T lymphocytes may have an involvement long before clinical symptoms of diabetes emerge. Evidence in this direction relies, in part, on successful treatment of recently diagnosed diabetic patients with cyclosporin, an immunosuppressive drug. Such treatment has been shown to prevent or cause remission of insulin-dependent diabetes mellitus in mice (Mori et al., *Diabetologia* 29:244–247 (1986)), rats (Jaworski et al., *Diabetes Res.* 3:1–6 (1986)), and humans (Feutren et al., *Lancet*, 11:119–123 (1986)). A clinical test to detect the presence of these humoral and cellular immunoreactions would allow the screening of individuals in a pre-diabetic state, which individuals could then be prophylactically treated with immunosuppressive drugs.

Current treatment of individuals with clinical manifestation of diabetes attempts to emulate the role of the pancreatic beta cells in a non-diabetic individual. Individuals with normal beta cell function have tight regulation of the amount of insulin secreted into their bloodstream. This regulation is due to a feed-back mechanism that resides in the beta cells that ordinarily prevents surges of blood sugar outside of the normal limits. Unless blood sugar is controlled properly, dangerous, even fatal, levels can result. Hence, treatment of a diabetic individual involves the use of injected bovine, porcine, or cloned human insulin on a daily basis.

Injected insulin and diet regulation permit survival and in many cases a good quality of life for years after onset of the disease. However, there is often a gradual decline in the health of diabetics that has been attributed to damage to the vascular system due to the inevitable surges (both high and low) in the concentration of glucose in the blood of diabetic patients. In short, diabetics treated with injected insulin cannot adjust their intake of carbohydrates and injection of insulin with sufficient precision of quantity and timing to prevent temporary surges of glucose outside of normal limits. These surges are believed to result in various vascular disorders that impair normal sight, kidney, and even ambulatory functions.

Both of these disease states, i.e., type I and type II diabetes, involving millions of people in the United States alone, preferably should be treated in a more regulated fashion. Successful transplants of whole isolated islets, for example, have been made in animals and in humans. However, long term resolution of diabetic symptoms has not yet been achieved by this method because of a lack of persistent functioning of the grafted islets in situ. See Robertson, *New England J. Med.*, 327:1861–1863 (1992).

For the grafts accomplished thus far in humans, one or two donated pancreases per patient treated was required. Unfortunately only some 6000 donated human pancreases become available in the United States in a year, and many of these are needed for whole pancreas organ transplants (used when the pancreas has been removed, usually during cancer surgery). Therefore, of the millions of diabetic individuals who could benefit from such grafts, only a relative handful of them may be treated given the current state of technology. If the supply of islet cells (including but not necessarily limited to beta cells) could be augmented by culturing the donated islets in cell culture, expanded populations would provide sufficient material to allow a new treatment for insulin-dependent diabetes.

In a similar fashion, the follicle cells of the human thyroid gland are highly specialized to respond to ambient levels of thyroid stimulating hormone, TSH, and to synthesize thyroglobulin, a very large complex protein that requires iodination for its activity. In response to TSH levels, thyroglobulin is secreted as tetra-iodo and tri-iodo thyronine ($T_3$), which are known collectively as the thyroid hormone, thyroxine. The thyroid cells of rats have been successfully cultured in media that allows the specialized functioning as well as the hormone dependence of these cells to be retained (Ambesi et al., *Proc. Natl. Acad. Sci. USA*, 77:3455–3459 (1980)); however, analogous cell cultures of human thyroid cells have not been successfully maintained. These rat cell cultures, called FRTL and FRTL-5, and their clonal variants have become the basis for clinical tests that seek to identify thyroid stimulating substances in the serum of patients with suspected thyroid disease. The FRTL/FRTL5 cell cultures originated from normal adult rat thyroid glands. These cell strains respond to thyrotropin (TSH) by releasing thyroglobulin (Tg), producing cyclic AMP (cAMP), trapping iodide, and growing. The TSH-dependent growth in FRTL and FRTL5 cells suggested a key role of the hormone as a mitogenic factor for thyroid cells; however, not all reports have confirmed this observation (see Westermark et al., *Proc. Natl. Acad. Sci. USA*, 76:2022–2026 (1979); Valente et al., *Endocrinology*, 112:71–79 (1983)). As to the role of cAMP, as a second messenger, it appears that components besides the modulation of cAMP production may be involved in TSH stimulatory effects (see, for example, Lombardi et al., *Endocrinology*, 123:1544–1552 (1988)). Whereas in genetically engineered FRTL5 cells a pseudophysiological rise of intracellular cAMP level is enough to stimulate cells proliferation (Hen et al., *Proc. Natl. Acad. Sci. USA*, 86:4785–4788 (1989)), normal thyroid cells cultured from other sources may not display the same behavior.

Other second messengers, besides cAMP, have been hypothesized to have a role in the regulation and action of thyroid cells; however, no clear empirical data support any such hypotheses (see, for example, Raspé et al., *Mol. Cell. Endocrin.*, 81:175–183 (1991)). An important role may also be played by autocrine (Takahoshi et al., *Endocrinology*, 126:7–36–7–45 (1990)) or indirect paracrine influences (Goodman and Rene, *Endocrinology*, 121:2131–2140 (1987)). Little can be recited definitively because the above-cited studies dealt with thyroid cells from different animal species or from human pathological samples so that discrepancies may be due to differences between species, to the various pathological conditions, or to adaptation of the cells to the various culture conditions used. The few studies on reportedly normal, non-transformed donor tissues have been to primary cultures, with very little evidence of in vitro cell proliferation (see, for example, Raspé et al., supra).

Thyroid pathologies, such as goiter, Grave's disease, Hashimoto's disease, adenomas, and carcinomas, involve impairment of thyroid function and, typically, excision of the thyroid itself. While the etiology of thyroid pathologies are not well understood, treatment post-excision focuses on a hormone-replacement-based therapy. If normal thyroid cells could be produced in culture in sufficient quantities, such expanded populations would provide sufficient material to allow a post-excision new treatment for these thyroid diseases.

When the thyroid gland is damaged or removed, often the parathyroid glands are also damaged or removed. While the function of the thyroid gland is rather successfully replaced by taking thyroid hormone by mouth, the parathyroid function is not easily replaced. The principal hormone product of the parathyroid gland is a protein hormone called parathormone that is not effective if taken by mouth. Parathormone interacts with vitamin D and regulates mineral metabolism, particularly calcium.

A similar situation exists with respect to the parotid glands. These glands are located in the angle of the jaw and are responsible for producing much of the saliva that lubricates the oral cavity. In particular, three major salivary proteins are secreted by the parotid gland; namely, lumicarmine, amylase, and gustin. The absence of the parotid secretions can result in xerostomia, or dry mouth, a common, clinically disturbing but not life-threatening disorder. Xerostomia affects all patients following X-irradiation of the oral cavity for treatment of oral cancers and many patients with Sjogren's syndrome. This disorder exacerbates symptoms of stomatitis, gingivitis, periodontitis, taste loss and tooth loss. Treatment of this symptom has been largely unsuccessful, consisting mainly of supplying oral moisturizers. If normal parotid cells could be produced in culture in sufficient quantities, such expanded populations would provide sufficient material to allow a new treatment for the xerostomic disorder.

Other cell types have been similarly refractory in being cultured long-term by conventional methods, particularly those of ectodermal or endodermal embryonic derivation. Among these other cell types are cells of the olfactory neuroblasts, prostate gland, lachrymal gland, cartilage, inner ear, liver, parathyroid gland, oral mucosa, sweat glands, hair follicles, adrenal cortex, urethra, bladder, many human tumors, and others. Additionally, primary human tumor cells have not been susceptible to propagation in culture, including those tumor cells of the thyroid, lung, cervix, epithelium (carcinoma), and pituitary and thyroid adenoma.

Some cell types, such as amniocytes and venous and arterial endothelium, have been cultured in vitro; however, the growth rates or the faithful retention of differentiated functions have not proven particularly efficacious. Growth rates of amniocytes in conventional media are such that the time required to grow the cells for purposes of diagnosis of some genetic disorders can result in providing information at a time point in the development of a fetus, for example, when the information can be acted upon only with the most dire of impact on the patient, or, perhaps, cannot be acted upon at all. Such growth rates have an economic impact, of course, with respect to the culturing of any of the aforementioned cells. To the extent the cultured cells themselves are products for surgical procedures, for example, skin cells applicable to burn victims, or for production of pharmaceuticals, the existence of techniques to cause cell culturing rates to increase results in a more plentiful and less costly supply of those cells.

The present invention attempts to meet many of these culturing needs. In particular, the present invention provides a novel culturing method and medium which are capable of producing an expanded culture of a wide variety of cells which have previously not been so cultured. Such cells include pancreatic islet cells, thyroid cells, parathyroid cells, parotid cells, tumor cells, and the other cell types discussed above. The present invention further seeks to provide certain aggregates of cells, such as pancreatic, thyroid, parathyroid and parotid cells, that have tissue-like qualities (referred to herein as "pseudotissues"), as well as the use of such pseudotissues for the treatment of various disorders, e.g., blood sugar concentration disorders, thyroid deficiencies, parathormone deficiencies and/or mineral dyscrasia, and xerostomia in mammals. The present invention also seeks to provide techniques for the use of the cultured cells for cytotoxicity assays of exogenous materials and to assess disease states of patients.

These and other features and advantages of the invention will be more readily apparent upon reading the following description of preferred exemplified embodiments of the invention and upon reference to the accompanying drawings, all of which are given by way of illustration only, and are not limitative of the present invention.

SUMMARY OF THE INVENTION

The present invention provides a method for producing an expanded non-transformed cell culture of a cell-type selected from the group consisting of glandular, neuroblast, liver, adrenal cortex, oral mucosa, cartilage, inner ear, urethra, and bladder cells, comprising the steps of: (a) preparing the cells by mincing a tissue that comprises the cells, thereby obtaining a substructure of the tissue or free cells; (b) concentrating the substructures or cells; (c) resuspending the concentrated substructures or cells in a culture medium capable of supporting sustained cell division; (d) incubating the culture; and (e) passaging the culture periodically. The culture medium preferably comprises a basal medium and an extract of hypothalamus, pituitary gland, or placenta. The present invention further provides a method of preparing clonal strains, which method comprises the steps of: (a) preparing a cell culture as described above; (b) growing the culture into a confluent layer of cells; (c) dissociating the cells; (d) inoculating the cells into another culture vessel that contains a conditioned medium for a first plating; (e) harvesting individual colonies of cells; (f) inoculating the colonies into another culture vessel for a second plating; and (g) passaging the resultant cells periodically.

The present inventive method is suitable for use with a variety of cells, including pancreatic, thyroid, parathyroid, and parotid cells, as well as many other types of cells.

The present invention also provides a culture medium which is used desirably with the present inventive method. The culture medium comprises a basal medium and an extract of tissue or components thereof such that the combination does not preclude sustained cell division by cultured cells that are derived from exocrine or endocrine glands. The basal medium is preferably Coon's Modified F12 Medium, while the tissue is preferably selected from the group consisting of hypothalamus, pituitary gland, and placenta.

The present invention additional provides expanded cell cultures of pancreatic endocrine cells, thyroid cells, and parotid cells and methods of using such cell cultures in diagnostic assays and in therapeutic treatments.

DETAILED DESCRIPTION OF THE INVENTION

Figure 1:
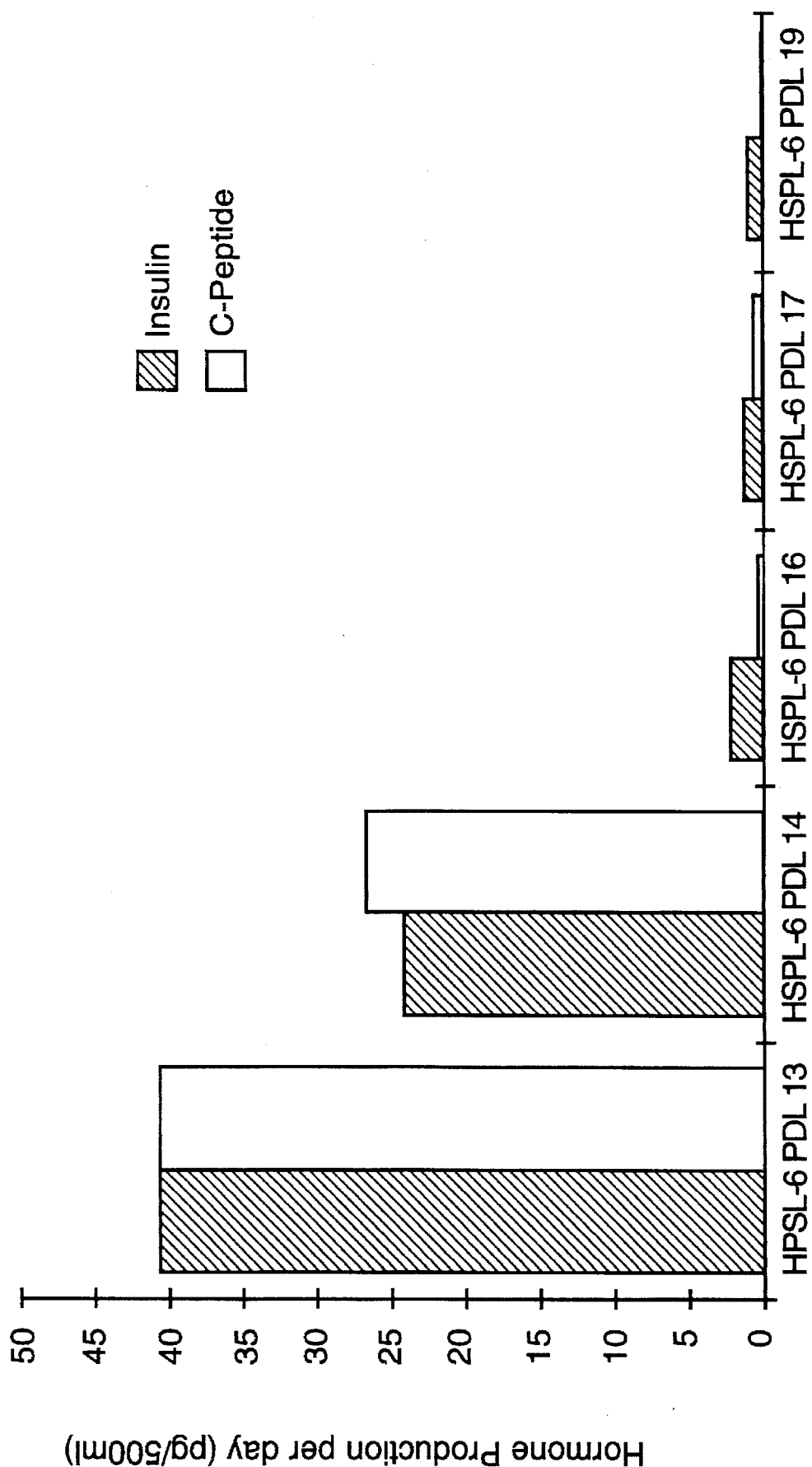
FIG. 1 is a graph that shows the accumulation of insulin and C-peptide in the medium of HPSL-6 cultured cells without glucose challenge.

The following detailed description of the invention is provided to aid those skilled in the art in practicing the present invention. This detailed description should not be construed to limit the present invention, as modifications and variations in the embodiments herein discussed may be made by those of ordinary skill in the art without departing from the spirit or scope of the present inventive discovery.

The present invention provides for a method for producing an expanded non-transformed cell culture of a cell-type selected from the group consisting of glandular, neuroblast, liver, adrenal cortex, oral mucosa, cartilage, inner ear, urethra, and bladder cells, comprising the steps of: (1) preparing said cells by mincing a tissue that comprises the cells, thereby obtaining cells or substructures of the tissue; (2) concentrating the cells or substructures; (3) resuspending the concentrated cells or substructures in a culture medium capable of supporting sustained cell division; (4) incubating the culture; and (5) passaging the culture.

The cell-types subjected to this procedure are derived from various tissues, can be of human origin or that of any other mammal, and may be of any suitable source, such as a whole pancreas, parotid gland, thyroid gland, parathyroid gland, prostate gland, lachrymal gland, cartilage, kidney, inner ear, liver, parathyroid gland, oral mucosa, sweat gland, hair follicle, adrenal cortex, urethra, and bladder, or portions or multiples thereof. The tissue is prepared using any suitable method, such as by gently teasing apart the excised tissue or by digestion of excised tissue with collagenase via, for example, perfusion through a duct or simple incubation of, for example, teased tissue in a collagenase-containing buffer of suitable pH and tonic strength. The prepared tissue then is concentrated using suitable methods and materials, such as centrifugation through ficol gradients for concentration (and partial purification). The concentrated tissue then is resuspended into any suitable vessel, such as tissue culture glassware or plasticware. The resuspended material may include whole substructures of the tissue, cells and clusters of cells. For example, such substructures may include islets and ducts in the case of pancreatic tissue and follicles in the case of thyroid tissue.

The initial culture of resuspended tissue cells is a primary culture. In the initial culturing of the primary culture, the cells attach and spread on the surface of a suitable culture vessel with concomitant cell division. Subsequent to the initial culture, and usually after the realization of a monolayer of cells in the culture vessel, serially propagated secondary and subsequent cultures are prepared by dissociating the cells of the primary culture and diluting the initial culture or its succeeding cultures into fresh culture vessels, a procedure known in the art as passaging. Such passaging results in an expanded culture of cells of the originating tissue. The cell culture is passaged at suitable intervals, such as about once a week or after about two to about three cell divisions of the cultured cells. Longer intervals of two to three weeks or shorter intervals of two to three days would suffice also. For passaging the cell cultures, a dilution of the cultured cells at a ratio of from about 1:2 to about 1:100 is used. Preferably, a ratio of from about 1:4 to about 1:50 is used. More preferably, a ratio of from about 1:4 to about 1:6 is used.

The concentrated prepared tissue, which may be in the form of free cells and/or clumps (where the clumps may constitute ordered substructures of the tissue) is resuspended at any suitable initial cell or presumptive cell density. Suitable cell densities range from about 100 cells to about 1000 cells per square centimeter of surface area of the culture vessel. Such cell densities for initial plating are best illustrated by identifying such parameters for specific cell systems, as follows.

For culturing pancreatic tissue cells, the concentrated islets are resuspended at any suitable initial islet density, such as at an initial islet density of from about 1 to about 700 islets per square centimeter of surface area of the culture vessel, which is equivalent to an initial islet density of from about 100 to about 50,000 islets per standard 100 mm diameter petri dish. In a preferred embodiment, the concentrated islets are resuspended at a density of from about 1 to about 70 islets per square centimeter of surface area of the culture vessel, which is equivalent to an initial islet density of from about 100 to about 5000 islets per standard 100 mm diameter petri dish. In a more preferred embodiment, the concentrated islets are resuspended at a density of from about 1 to about 7 islets per square centimeter of surface area of the culture vessel, which is equivalent to an initial islet density of from about 100 to about 500 islets per standard 100 mm diameter petri dish. In another more preferred embodiment of this method, the concentrated islets are resuspended at a density of from about 3 to about 7 islets per square centimeter of surface area of the culture vessel, which is equivalent to an initial islet density of from about 250 to about 500 islets per standard 100 mm diameter petri dish.

For culturing thyroid tissue cells, the concentrated cells and fragments of follicles are resuspended at any suitable initial density, such as at an initial cell density of from about $10^4$ cells to about $10^6$ cells per 100 mm diameter petri dish (Falcon, Becton Dickinson, Lincoln Park, N.J.). In a preferred embodiment, the concentrated thyroid cells are resuspended at a density of from about $6 \times 10^4$ cells to about $5 \times 10^5$ cells per 100 mm diameter petri dish. In a more preferred embodiment, the concentrated thyroid cells are resuspended at a density of about $8 \times 10^4$ cells to about $3 \times 10^5$ cells per 100 mm diameter petri dish.

The method for producing an expanded cell culture depends on the use of a culture medium that comprises a suitable basal medium and a suitable extract of a suitable tissue, the combination of which is designed not to preclude sustained cell division by the cultured cells derived from the aforementioned tissues, including exocrine and endocrine glands. Serum or components derived therefrom typically are also included in the mixture. Components of the tissue extract may be used in place of the crude or partially purified tissue extract.

Basal media that may be used include those commercially available from Sigma Chemical Co., Life Technologies, Inc., or BioWhittaker Co. Any basal medium may be used provided that at least magnesium ion, calcium ion, zinc ion, bicarbonate ion, potassium ion, and sugar levels can be manipulated to a lower or higher concentration in the resultant medium; in particular, the magnesium ion, calcium ion, bicarbonate ion, and D-glucose levels are required at a lower concentration, zinc ion is required at the same or higher concentration, and potassium ion is required at the same or lower concentration than is usual in standard basal media.

Preferred levels of magnesium ion, as contributed by suitable magnesium salts, such as $MgSO_4.7H_2O$ and $MgCl_2.6H_2O$, are between 60 and 240 mg/L; more preferred levels of magnesium salts are between 100 and 150 mg/L. Preferred levels of calcium ion, as contributed by suitable calcium salts, such as $CaCl_2.2H_2O$, are between 25 and 200 mg/L; more preferred levels of calcium ion are between 40 and 125 mg/L. Preferred levels of zinc ion, as contributed by suitable zinc salts, such as $ZnSO_4.7H_2O$, are between 0.1 and 0.5 mg/L; more preferred levels of zinc ion are between 0.12 and 0.40 mg/L; yet more preferred levels of zinc ion are between 0.15 and 0.20 mg/L. Preferred levels of ascorbic acid are between 30 and 125 mg/L; more preferred levels of ascorbic acid are between 40 and 100 mg/L. Preferred levels of bicarbonate ion, as contributed by suitable bicarbonate salts, such as sodium bicarbonate, are between 175 and 700 mg/L; more preferred levels of bicarbonate ion are between 300 and 400 mg/L. Preferred levels of potassium ion, as contributed by suitable potassium salts, such as potassium chloride, are between 100 and 400 mg/L; preferred levels of potassium ion are between 200 and 325 mg/L; most preferred levels of potassium ion are between 210 and 250 mg/L. Preferred levels of sugar, as contributed by a suitable sugar, such as D-glucose, are between 400 and 1800 mg/L; more preferred levels of sugar are between 600 and 1200 mg/L; most preferred levels of sugar are between 800 and 1000 mg/L. Preferred levels of human placental lactogen are between 3 and 15 µg/ml; more preferred levels of human placental lactogen are between 4 and 13 µg/ml; most preferred levels of human placental lactogen are between 8 and 12 µg/ml. Preferred levels of insulin, as contributed by a suitable naturally-isolated, clonally-derived, or synthesized insulin, such as isolated bovine sodium-insulin, are between 50 and 20,000 ng/ml; more preferred levels of insulin are between 100 and 10,000 ng/ml; most preferred levels of insulin are between 500 and 5,000 ng/ml.

One basal medium that can be used preferably is Coon's Modified F12 Medium (Coon et al., Proc. Natl. Acad. Sci. U.S.A., 86, 1703 (1989)), which is available from BioWhittaker Co., Walkerville, Md., or prepared according to the formula provided in Example 1.

The tissue extracts that may be used to prepare the present inventive culture medium include any suitable tissue that contains growth factors. Such tissues preferably include at least one of hypothalamus, pituitary gland, and placenta. As noted above, suitable components of a tissue extract, such as a partially or wholly purified solution containing suitable growth factors, or synthetic varieties thereof, may be used in place of the whole tissue extract, such as human placental lactogen in place of human placental extract. Such suitable components of a tissue extract may also be used in addition to the whole tissue extract, such as human placental lactogen plus human placental extract.

Serum is used at levels lower than those typically used by practitioners of the relevant art. For example, typical cell culture media use 10% to 20% fetal bovine serum, whereas the medium of the present invention uses less than 10% serum and generally from about 2% to about 6% serum. The preferred concentration of serum in the medium of the present invention is from about 3% to about 5%. The more preferred concentration of serum in the medium of the present invention is about 4%. Sources of sera include bovine fetuses and new born calves, and equine, porcine, ovine, and human fetuses and adults. Preferably, bovine fetal serum is used. Also, suitable components of sera, such as a partially or wholly purified solution derived from sera containing suitable growth factors, may be used in place of the whole serum. Suitable growth factors provided in serum may also be produced synthetically and may thereby replace the need for serum.

The preferred culture media are Coon's 4506.035 and Coon's 4506.07 media, as defined in Example 1. Coon's 4506.035 and Coon's 4506.07 media contain lower calcium ion ($Ca^{++}$) concentration, lower added serum concentration (4% versus 10–20% fetal bovine serum), and a relatively high concentration of growth factors as provided by the tissue extract components and human placental lactogen, as compared to Coon's modified F12 Medium from which these media can be prepared. Although fibroblasts typically overgrow cultures of glandular cells, such fibroblast cells, which are commonly co-purified with islet cells, for example, do not overgrow cultures in Coon's 4506.035 or 4506.07 medium when they are maintained in continuous, serial passage. Using Coon's 4506.07 medium, for example, fibroblasts grow 25–50% slower than in a conventional medium, such as 10% Fetal Calf Serum in Dulbeco's Modified Eagle's Medium.

The mass cultures of islets grown in Coon's 4506.035 or 4506.07 medium, in effect, become enrichment cultures for the endocrine cells of the islets. This failure of endogenous fibroblasts to overgrow and crowd out the functional endocrine cells is important in the success of cultures of pancreatic endocrine cells of the present invention as compared to earlier attempts to grow these cells. Similarly, this feature is important for growth of the other mentioned cell types.

The present invention also provides for a method for preparing clonal strains from each of the cell cultures discussed herein, including, for example, the pancreatic endocrine cell culture discussed herein, comprising the steps of: (1) preparing a cell culture according to the procedure outlined above; (2) growing the culture; (3) dissociating the cells; (4) inoculating the cells into another culture vessel for a first plating; (5) harvesting individual colonies of cells; (6) inoculating the colonies into another culture vessel for a second plating; and (7) passaging resultant clonal cell strains periodically.

A culture of cells may be used for preparing clonal strains upon having grown into a confluent layer of cells, or the culture may be used prior to having reached confluence. Dissociation may be effected using any suitable means, such as by trypsin or some other proteolytic treatment. Any suitable density of cells per square centimeter of surface area of a culture vessel can be used for the first plating, such that the growth of individually isolable colonies is promoted. Preferably, between about 3 and about 150 cells per square centimeter of surface area of a culture vessel is used; more preferably, between about 7 and about 70 cells per square centimeter is used.

For the preparation of clonal strains, a conditioned medium is required for the first plating described immediately above, wherein the medium may be conditioned homologously (i.e., by the same type of cells that are to be cloned) or heterologously (i.e., by cells other than the type that is to be cloned). The conditioned medium can be prepared by the steps of: (1) incubating cultured cells, as prepared according to the procedure described herein; (2) harvesting the medium; and (3) sterile filtering the resultant conditioned medium.

The cell density used for preparation of the conditioned medium can range from very few cells per square centimeter of surface area of a culture vessel to near confluence. The length of time of incubation required is inversely dependent on the cell density. In essence, a suitable concentration of excreted cell products from the cells forms necessary ingredients of conditioned medium, which concentration is reached more quickly with the greater number of cells incubated per unit volume of culture medium. It is necessary that the cells grow; thus any density that is less than confluence will suffice to prepare the conditioned medium. Preferably, the cell density ranges from about $5 \times 10^3$ to about $5 \times 10^4$ cells per square centimeter of surface area of a culture vessel, where the period of incubation ranges from about 18 hours to about 24 hours. In accordance with the aforementioned inverse relationship, if fewer cells are incubated, then a longer period of incubation is required; if more cells are plated, then a shorter period of incubation is required.

As regards the amount of culture medium in which the cells are incubated, the culture vessel may contain any suitable amount of culture medium and preferably should contain from about two to about four milliliters per $10^6$ cells. Preferred culture media include Coon's 4506.035 and Coon's 4506.07.

Harvesting of the conditioned medium is undertaken using any suitable means, such as pouring off or aspirating the medium into a suitable container, such as a flask. Sterile filtering of the harvested medium is undertaken using any suitable means, such as passing the medium through a suitable ultrafiltration membrane while under pressure. Alternatively, the medium may be filtered in a diafiltration process known to the art, also using membrane filters.

For inoculation of the first plating in the procedure for preparation of clonal strains, the sterile filtered conditioned medium is diluted to make it suitable for promoting growth of the inoculum. Preferably, three to five parts of the conditioned medium are diluted with one to three parts of a suitable culture medium. More preferably, about two parts of the conditioned medium are diluted with about one part of a suitable culture medium.

Individual colonies that form in the first plating are harvested after a suitable number of population doublings, which colonies therefore comprise a suitable number of cells. Preferably, the colonies are harvested after from about seven to about fifteen population doublings, at which point the colonies comprise from about 128 cells to about 32,000 cells. More preferably, the colonies are harvested after from about nine to about twelve population doublings, at which point the colonies comprise from about 500 to about 4,000 cells.

Inoculation for the second plating may be accomplished using any suitable starting cell density. The number of cells to be used is limited by the amount included in a selected colony; thus the plating density here is altered by changing the size of culture vessel and the amount of culture medium. The densities are similar to those preferably used for production of conditioned medium. Standard culture vessels of 30 mm diameter petri plates or microtiter plates (which have 5 mm diameter wells), for example, may be used to provide the appropriate ratio of surface area to number of cells in an inoculum.

Preferably from about one to about three parts of the conditioned medium is diluted with from about one to about three parts of the culture medium for feeding the cells of the first plating and the cells of the second plating. More preferably, about one part of the conditioned medium is diluted with about one part of the culture medium for feeding the cells of the first plating and the cells of the second plating.

Passaging of the cloned culture is accomplished with the same method as used to passage the primary and serially propagated cultures described above. The medium used when passaging the cloned strain of cells may be any suitable one as described above for the initial plating of islet cell preparations for primary cultures. Although conditioned medium may be used for passaging the cloned culture, a fresh medium is preferred.

An objective of the procedures described hereinabove is to isolate diploid, non-transformed cell cultures of various cell types that are capable of sustained cell division, wherein each culture contains a single cell type or related cell types. This objective has been accomplished using pancreatic tissue, thyroid tissue, parathyroid tissue, and parotid tissue, all of human origin, although such tissues derived from other mammals, such as dogs or horses, could be used as well. Such cultures also gave rise to cultures of cells that were derived from a single progenitor cell. Hence, pancreatic endocrine and duct, thyroid, parathyroid and parotid cells are not post-mitotic, at least when stimulated using the present inventive culture medium. The cells in culture remained diploid and retained other characteristics (presented below in Examples 5, 12 and 13, for example) that indicate that the pancreatic endocrine and duct, thyroid, and parotid cell cultures, for example, of the present invention were not transformed to a premalignant state. It has been also noted that cultures that were started with partially purified pancreatic islets, for example, composed of not only alpha, beta, delta, and duct pancreatic cells but also fibroblasts, macrophages, etc., were populated preponderantly by pancreatic endocrine cells using the medium of the present invention. Apparently, the medium of the present invention selects in favor of the pancreatic endocrine cells and against the other cells that are apparently co-purified with pancreatic islets.

As described in detail below, the pancreatic endocrine cell cultures of the present invention can be used as the basis for assays whose purpose is to identify cytotoxic agents of any source that are directed at islet cells. Similarly, thyroid cells, parotid cells, and other cells may be used analogously. Cytotoxicity, in general, is measured by exposing cell cultures to dilutions of a suspected toxic agent and, at some later time, assessing the number of killed or dead cells. With the advent of functionally differentiated human cells, a novel and more subtle assay is possible. In addition to monitoring dead cells, one can quantitate the ability of the suspected toxic substance(s) to interfere with normal physiological functions, e.g., to interfere with the ability of human beta cells in culture to respond to changes in the ambient glucose concentration by secreting insulin. An assay of this kind allows evidence of non-lethal but nevertheless toxic responses that might interfere with either the glucose-sensing process or the insulin-secretion process including the pre-insulin processing step evidenced by C-peptide release. Changes in the shape of the glucose concentration versus insulin secretion curves can indicate such impairment of normal physiological function, and measurements using established analytical procedures, like RIA, can quantitate both insulin secretion and C-peptide release into the medium.

Accordingly, the cultured cells of the present invention, which exhibit the characteristics of normal human cells, may be used in tests designed to detect the presence of cytotoxic agents of any kind, such as are used in the food industry, pharmaceutical industry, cosmetic industry, and other industries. In the area of medical diagnostics, such tests include clinical assays designed to detect certain autoantibodies or T-lymphocytes in the blood or tissues of patients with diabetes or possible diabetes. Such autoantibodies or T lymphocytes would be identified by their ability to interact with the cultured cells or to foster cytotoxic reactions in them or upon them.

This diagnostic assay comprises exposing a diploid cell culture of pancreatic endocrine cells that is capable of cell division to a chemical or sample of bodily fluid and assessing the effects of the exposure of the cells. The diploid cell culture is as described above, and may originate from any mammal; preferably the cell culture originates from a human. By exposure, it is intended that a tested chemical is put into solution and then diluted into the culture medium in which the test cells are incubating. Similarly, a suitable bodily fluid, such as blood serum, spinal fluid, mucous, etc., would be tested by diluting it into the culture medium in which the test cells are incubating. Serial dilutions of the test samples and positive and negative controls would also be included in this procedure. Assessment of the effect of the chemical or bodily fluid diluted into the culture medium of a test culture can be accomplished using any suitable means, such as by tracking vital signs of the culture using methods known in the art. Such trackable vital signs include population doubling time and metabolic rate. Preferably, cultured pancreatic beta cells challenged by inclusion of a suspected cytotoxin in the culture medium are assessed for response to changes in the ambient glucose concentration using methods known in the art. The primary response for assessment is insulin-secretion and the prior step of processing of pre-insulin and the resultant release of C-peptides.

The donated human pancreas cells used in the diagnostic test assay for autoantibodies and cytotoxic T-cells are taken preferably from individuals with the HLA markers associated with high incidences of IDDM. Among these markers are the HLA Class II antigens DR-3, DR-4, DW-3, DW-4 and B-8, B-15, which are associated with greatly increased risk of developing IDDM.

The donated human pancreas cells used in preparing pseudotissues for grafting for the purpose of regulating blood sugar levels are preferably taken from individuals with the HLA markers that are rarely if ever associated with development of IDDM. Among these are the HLA Class II antigens DR-5, DR-2, BW-2, BW-3, BW-8 and A-11.

Similarly, another preferred aspect of the present invention relates to cultured thyroid cells challenged by inclusion of a suspected cytotoxin in the culture medium, the toxicity of which is assessed by response of the cultured cells to ambient TSH concentrations using methods known in the art. The primary response for assessment can be cAMP production and iodide uptake. Analogous cytoxicity tests involving other cell types that are newly culturable by use of the present inventive cultures are also aspects of the present invention.

The present invention also concerns therapeutic methods involving the use of the present inventive cultures. For example, the present invention provides a method of altering blood sugar levels comprising administering to a mammal a cell culture of pancreatic endocrine cells. The cell culture used for altering blood sugar levels may be a primary cell culture of pancreatic endocrine cells, or a serially passaged culture thereof. Preparation of such a cell culture is as described hereinabove. The cell culture used may also be a clonal cell culture of pancreatic endocrine cells, preparation of which is as described hereinabove also. The cultured pancreatic endocrine cells of the present invention include beta cells that secrete insulin in response to glucose concentration.

The method of altering blood sugar levels may be accomplished using cultured pancreatic endocrine cells in a tissue-like form. Such cultured pancreatic endocrine cells, either as individual beta cells or in combination with other cell types, can form coherent aggregates spontaneously or by culturing techniques known in the art. Such coherent aggregates are termed "pseudoislets" herein. Preferably, pseudoislets are embedded in a suitable biocompatible matrix, such as collagen, using methods known in the art. The cultured pancreatic endocrine cells also may be formed into coherent aggregates by co-incubation with a suitable biocompatible material, such as collagen, whereby the cells are in the form of free suspensions prior to the co-incubation. The coherent aggregate of cells formed by either method is termed a "pseudotissue." Pseudotissues form a biologically compatible graft that can be implanted into a mammal, and therein function to alter blood sugar levels.

Primary, secondary and subsequent, or clonal cultures of pancreatic endocrine cells, or combinations thereof prepared according to the methods described herein, and exemplified below, may be used in such pseudotissues. The method involves grafting pancreatic endocrine cells as a pseudotissue, for example, into a mammal where the pseudotissue becomes vascularized and responds to the blood glucose levels in the host mammal by secreting insulin when the blood glucose levels attain a sufficiently high level. Vascularization of the pseudotissue appears to be important in that in those experiments where the pseudotissue did not become vascularized, blood sugar levels were not regulated. Similarly, delayed vascularization of a pseudotissue appeared to impair the ability of the pseudotissue to regulate blood sugar levels. A practical demonstration of successful pseudotissues according to the present invention is illustrated in Example 10 below in an experimental diabetic mouse system. However, the same approach can be used to treat aberrant blood sugar levels in other mammals as well, most particularly humans, dogs, and horses.

The present invention also concerns a method of providing thyroid hormones or parathormone comprising administering to a mammal a cell culture of thyroid or parathyroid cells, respectively. The cell culture used for providing thyroid hormones or parathormone may be a primary cell culture of thyroid or parathryoid cells, or a serially passaged culture thereof. Preparation of such a cell culture is as described hereinabove. The cell culture used may also be a clonal cell culture of thyroid or parathyroid cells, preparation of which is as described hereinabove also. The cultured thyroid or parathyroid cells of the present invention include thyroid follicle cells that secrete thyroid hormones in response to TSH concentration and parathyroid tissue that secretes parathormone.

The method of providing thyroid hormones or parathormone may be accomplished using cultures of appropriate cells derived from the respective glands that are formed into a tissue-like form. Such cultured gland cells, either as individual follicle cells, in combination with other cell types, or dissociated gland cells, can form coherent aggregates spontaneously or by culturing techniques known in the art. Such coherent aggregates are termed "thyroid pseudotissue" or "parathyroid pseudotissue," as appropriate, herein. Preferably, such pseudotissues are embedded in a suitable biocompatible matrix, such as collagen, using methods known in the art. The cultured gland cells also may be formed into coherent aggregates by co-incubation with a suitable biocompatible material, such as collagen, whereby the cells are in the form of free suspensions prior to the co-incubation. The coherent aggregate of cells formed by either method is termed a "thyroid pseudotissue" or a "parathyroid pseudotissue," as appropriate. Thyroid or parathyroid pseudotissues form a biologically compatible graft that can be implanted into a mammal, and therein function to provide thyroid hormone or parathormone, depending on the derivation of the cells that form the pseudotissue used.

Primary, secondary and subsequent, or clonal cultures of thyroid or parathyroid cells, or combinations of primary, secondary and subsequent, or clonal cultures prepared according to the methods described herein, and exemplified below, may be used in such thyroid or parathyroid pseudotissues. The method involves grafting the appropriate cells as a thyroid pseudotissue, for example, into a mammal where the thyroid pseudotissue becomes vascularized and responds to the blood TSH levels in the host mammal by secreting thyroid hormones, producing cAMP, and intaking iodide when the blood TSH levels attain a sufficiently high level. Similarly, a parathyroid pseudotissue may be grafted into a mammal where the pseudotissue becomes vascularized and responds to blood calcium levels, for example, by secreting parathormone.

Collagen is ordinarily extracted under acid conditions and, if subsequently neutralized, remains liquid at 4° C. At 37° C., neutralized solutions of collagen irreversibly form into a gel. Thus, if a cell suspension is made in a collagen solution at 4° C. and then incubated at 37° C., the cells will become embedded in a gel. At high densities (1:1 collagen:cells), one variety of pseudotissue is formed that can be cast and formed into shapes suitable for implantation at various sites (e.g., as a sheet for implantation subcutaneously). Alternatively, the cells may first be allowed to reaggregate into clusters of from 25–250 cells (pseudoislets), and then these clusters in turn may be embedded in a collagen gel as above, thereby forming another variety of pseudotissue. In either case, the use of a collagen gel is known to promote vascularization and healing of graft cells into the tissues of the host animal.

The following examples are illustrative of the preparation and use of the products and methods of the present invention. As such, the following examples further illustrate the present invention but, of course, should not be construed as in any manner limiting its scope.

EXAMPLE 1

This example illustrates the preparation of media suitable for growing tissue cells in culture. In particular, Coon's 4506.07 and 4506.035 media are described.

Growth media in accordance with the present invention were prepared by combining Coon's Modified F12 Medium containing no added calcium and reduced KCl with mixtures of tissue extracts. The formula of Coon's Modified F12 Medium is recited below.

The tissue extracts were made as described in Coon et al., *Proc. Natl. Acad. Sci. U.S.A.*, 86, 1703 (1989). Frozen tissue was homogenized in a Waring blender with a two-fold dilution (1:2 wt/vol) aqueous HEPES buffer (200 mM adjusted to pH 7.2 with NaOH). The tissue homogenate thus formed was refrigerated for 30 minutes in a refrigerator (4° C.), remixed by a short period of blending, and refrigerated for an additional 30 minutes. After remixing as described, two refrigerated ($\leqq 6°$ C.) centrifugations were performed. First, a low speed centrifugation for 1 hour at approximately 30,000×g of the homogenate was carried out. The supernatant fluid was then decanted and immediately recentrifuged for 1 hour at approximately 150,000×g in an ultracentrifuge. When the supernatant fluid (the extract) was aspirated from the centrifuge tubes, the most dense material at the bottom of the tube was carefully prevented from contaminating the final product because this material contains substances that make sterile filtration very difficult. The extracts were frozen quickly by submersing partly filled plastic tubes in liquid nitrogen. Extracts were made in this way of bovine hypothalami and whole pituitary glands. Human placentae were also extracted using this method; however, because the placenta is such a tough and fibrotic tissue, it was neneccessary first to grind or cut up the tissue before the homogenization step.

After the preparation of the ingredients was complete, they were combined in a manner known in the art to provide media having the below-indicated final concentrations of each component. Empirical observation demonstrated that certain of the ingredients of the Coon's 4506.035 and 4506.07 Media could be varied within certain ranges, or have alternative concentrations, as indicated in the table below. One ingredient, Na-Insulin, was determined empirically to be useful over a range of concentrations, as indicated in the table; the usual concentration used for the present inventive growth medium is indicated in a footnote below the chart. Unless otherwise noted, all values are in mg/L units.

| | Coon's▲ mF12 | Coon's 4506.035 | Coon's 4506.07 |
|---|---|---|---|
| L-Arginine HCl | 420 | 420 | 420 |
| L-Histidine Hcl | 42 | 42 | 42 |
| L-Isoleucine | 8 | 8 | 8 |
| L-Leucine | 26 | 26 | 26 |
| L-Lysine Hcl | 73 | 73 | 73 |
| Glycine | 16 | 16 | 16 |
| L-Methionine | 9 | 9 | 9 |
| L-Phenylalanine | 10 | 10 | 10 |
| L-Serine | 21 | 21 | 21 |
| L-Threonine | 24 | 24 | 24 |
| L-Tryptophan | 4 | 4 | 4 |
| L-Tyrosine | 11 | 11 | 11 |
| L-Valine | 23.4 | 23.4 | 23.4 |
| L-Cysteine | 0 | 0 | 0 |
| L-Cystine.HCl.H$_2$O | 70 | 70 | 70 |
| L-Asparagine.H$_2$O | 30 | 30 | 30 |
| L-Proline | 70 | 70 | 70 |
| L-Alanine | 18 | 18 | 18 |
| L-Aspartic acid | 26 | 26 | 26 |
| L-Glutamic acid | 30 | 30 | 30 |
| Sodium pyruvate | 220 | 220 | 220 |
| Putrescine.2HCl | 0.30 | 0.3 | 0.3 |
| Biotin | 0.07 | 0.07 | 0.07 |
| D-Ca-Pantothenate | 0.50 | 0.5 | 0.5 |
| Niacinamide | 0.04 | 0.04 | 0.04 |
| Linoleic acid | 0.09 | 0.09 | 0.09 |
| Pyridoxine.HCl | 0.06 | 0.06 | 0.06 |
| Thiamine.HCl | 0.285 | 0.285 | 0.285 |
| Riboflavin | 0.04 | 0.04 | 0.04 |
| Folic acid | 1 | 1 | 1 |
| Vitamin B-12 | 1 | 1 | 1 |

-continued

| | Coon's▲ mF12 | Coon's 4506.035 | Coon's 4506.07 |
|---|---|---|---|
| Thioctic acid | 0.2 | 0.2 | 0.2 |
| myo-Inositol | 36 | 36 | 36 |
| Ascorbic acid | 45 | 45–100◊ | 45–100◊ |
| Choline.HCl | 13.8 | 13.8 | 13.8 |
| Thymidine | 0.7 | 0.7 | 0.7 |
| Hypoxanthine | 4 | 4 | 4 |
| NaCl | 7530 | 7530 | 7530 |
| KCl | 305 | 230 | 230 |
| Na$_2$HPO$_4$.7H$_2$O | 250 | 250 | 250 |
| KH$_2$PO$_4$ | 68 | 68 | 68 |
| MgSO$_4$.7H$_2$O | 104 | 60 | 60 |
| MgCl$_2$.6H$_2$O | 106 | 60 | 60 |
| CaCl$_2$.2H$_2$O | 165 | 53 | 105 |
| CuSO$_4$.5H$_2$O | 0.002 | 0.002 | 0.002 |
| ZnSO$_4$.7H$_2$O | 0.15 | 0.15 | 0.15 |
| FeSO$_4$.7H$_2$O | 0.80 | 0.80 | 0.80 |
| D-Glucose | 2000 | 1000 | 1000 |
| NaHCO$_3$ | 2500 | 350 | 350 |
| L-Glutamine | 292 | 292 | 292 |
| Phenol red | 1.25 | 1.25 | 1.25 |
| Na-Insulin (bovine) | 0 | 100 to 10,000 ng/ml* | 100 to 10,000 ng/ml* |
| Transferrin (bovine) | 0 | 5 μg/ml | 5 μg/ml |
| Tri-iodothyronine (T$_3$) | 0 | 40 pg/ml | 40 pg/ml |
| Selenous acid | 0 | 2.5 ng/ml | 2.5 ng/ml |
| Hydrocortisone | 0 | 3.5 ng/ml | 3.5 ng/ml |
| Gentamycin SO$_4$● | 0 | 50 μg/ml● | 50 μg/ml● |
| Fetal Calf Serum | 0 | 40 ml/L | 40 ml/L |
| Pituitary Extract | 0 | 50 μg/ml♦ | 50 μg/ml♦ |
| Hypothalamus Extract | 0 | 115 μg/ml♦ | 115 μg/ml♦ |
| Human Placental ◻ Extract | 0 | 50 μg/ml♦ | 50 μg/ml♦ |
| Human Placental ◻ Lactogen | 0 | 10 μg/ml | 10 μg/ml |

*Usual concentration is 300 ng/ml.
▲Coon's modified F12 medium.
●Optional component (antibiotic).
◻Either Human Placental Extract or Human Placental Lactogen were used; not both.
♦Based on protein content of extract.
◊Usual concentration is 45 mg/L.

EXAMPLE 2

This example illustrates the preparation of partially purified islets of Langerhans from explanted pancreatic tissue, and the primary culturing of partially purified islets to provide mass cultures of pancreatic endocrine cells.

Pancreases or portions thereof were obtained from adult human donors believed to have had normal pancreatic function. The pancreatic tissue used herein was received from a total of 11 adult human patients, both males and females, and collected by two medical transplant groups based in Milan, Italy and St. Louis, Mo. No differences were noted in the culturing or glandular characteristics of cultured cells derived from these sources.

Partially purified pancreatic islets of Langerhans of the Milan and St. Louis pancreatic tissues were provided by Drs. Valerio Di Carlo, Guido Pozza, and Carlo Socci, San Raffaele Hospital, Milan, Italy and by Drs. Scharp and Lacy of Washington University Medical School, Barnes Hospital, St. Louis, Mo. Established methods were used to prepare the islets, including mincing the pancreatic tissue or perfusing the whole pancreas via the common duct with a solution of collagenase, and final separation on ficol step gradients to produce concentrated populations of islets largely purified from other pancreatic tissue components. In this manner approximately 300,000 islets were prepared of which 5,000–10,000 were used.

The isolated islets were plated one day after preparation directly into a culturing vessel, which was tissue culture grade glassware or plasticware (Falcon and Corning brands were used with equal success), using Coon's 4506.035 or Coon's 4506.07 Medium (described in Example 1). Between 300 and 500 islets were placed into each standard 100 mm diameter petri plate, where they attached to the surface. The cells of the islets grew and spread out on the culture vessel surface, and after a period of time (usually two to three weeks), they were trypsinized in standard fashion (with or without EDTA or EGTA chelation) to dissociate them from the vessel surface and from each other.

EXAMPLE 3

This example illustrates maintenance of the mass pancreatic endocrine cell cultures by passaging.

The mass primary cultures produced by the many islets (100 to 500 islets per standard 100 mm diameter petri plate) growing and spreading in the same culture vessel were maintained in log phase growth by trypsinizing them and diluting them 4 to 6 fold into new vessels weekly. Long term serial passages grew at a rate of about 2.5 population doublings per week. The cells so cultured were observed to become enriched for endocrine cells of the islets over other cells that were co-purified with the islets, such as fibroblasts and capillary endothelial cells. After 10 passages, for example, HPSL-8 cultures included very few or no fibroblasts (judging by cell morphology). Moreover, no evidence of capillary endothelial cells was found using an indirect immunofluorescence assay for factor-VIII-related-antigen.

EXAMPLE 4

This example illustrates preparation of conditioned medium.

Both primary cultures and the mass cultures made by serial passage of the primary cultures described in Example 2 above were used separately to produce a derivative medium, called conditioned medium (CM). CM was used for cloning the cells from the primary culture plates, as well as from the serially propagated passage plates. CM was made by adding to culture vessels containing about $5 \times 10^4$ cells per square centimeter ($cm^2$) of vessel surface area and sufficient Coon's 4506.07 medium to result in about 2.75 ml medium per $10^6$ cells, then incubating them for 20–25 hours, harvesting the medium and sterile filtering (using a Millipore 0.22 µm membrane, or equivalent) immediately before use.

EXAMPLE 5

This example illustrates a method for preparation of a clonal strain of cultured pancreatic endocrine cells and sets forth the results of an analysis of the cloned strains.

Mass cultures of pancreatic endocrine cells prepared according to Example 2 were used as a source of pancreatic endocrine cells, which were plated in a sequence of two platings. Conditioned media, as prepared according to Example 4, were diluted two parts CM with 1 part fresh Coon's 4506.07 Medium for the first plating. Suspensions of freshly trypsinized cells were plated at densities of 500, 1000, 2000, and 5000 cells per standard 100 mm diameter plastic petri plate. Thereafter, the clone cultures were fed twice weekly with freshly prepared CM diluted 1:1 with fresh Coon's 4506.07 Medium.

Well isolated, circular, homogeneous colonies resulted at efficiencies of from 0.03% to 0.7%. Such colonies were selectively dissociated by trypsinization when they reached approximately 1000 cells, using glass cloning cylinders and silicone hi-vac grease to affix the cylinders to the petri plates. After trypsinization had liberated the cells from the plate, the cloned (colony purified) cells were removed from the cylinders with glass or plastic capillary pipettes together with a small amount of the trypsin solution and plated in standard 60 mm diameter plasticware petri plates in CM diluted 1:1 with fresh Coon's 4506.07 Medium as before. When these cells had grown to confluence, the whole plate of cells was dissociated by trypsinization, diluted 1:6 or more, and transferred into fresh plates for subculture. The clonal cell strains thus established were subsequently fed twice weekly with a complete exchange of fresh 4506.07 growth medium without further need for CM. Cloned cell strains cultured in this way were maintained for 25 to 30 passages without signs of senescence or other failure of cell division, and without any overt sign of transformation or genetic adaptation to continuous cultivation. Aliquots of these populations were frozen for archival storage and the remaining cells were characterized using: (1) fluorescence immunocytochemistry (employing a double antibody technique, wherein the second antibody and purified hormone blocking controls were negative); and (2) RIA for insulin or C-peptide (indicators of beta cells), glucagon (indicator of alpha cells), and somatostatin (indicator of delta cells).

Results from these assays indicated that some of the cells derived from the human pancreas that divide in Coon's 4506.07 medium may have partially reverted to pluripotent cells that, in spite of clonal purification, produce populations of cells that contain at least three of the islet cell types: alpha, beta, and delta cells. In one assay, the cloned population showed clearly positive reactions (concentrated in the intracellular granules) indicating that the population was comprised of 20–25% beta cells, 10–15% alpha cells, and 5% delta cells. The remaining cells were either negative or weakly positive for staining for these three cell types. In other cell strains, the result was that the majority of cells stained diffusely for each of these products. All of the cells in all of the clonal populations were strongly positive for the neural and neuroendocrine marker, neuron specific enolase (NSE), and most of the cells were strongly positive for a marker for secretory cells of neuroendocrine systems, chromogranin A. Some clones of human pancreatic endocrine cells therefore can produce at least three of the cell types found in the normal adult, non-dividing islets of Langerhans.

In a similar experiment, clonal strains of human pancreatic islet cells showed specialization. Two clones of 27 tested, named HPSL-SU and HPSL-SD, apparently represented delta cells because when these cloned cultures were incubated for 24 hours in medium with no insulin and high (20 mM) glucose, they respectively produced 570 and 116 pg/ml of somatostatin (a distinctive hormonal product of delta cells). In high insulin (15 µg/ml) and low glucose (2.5 mM) medium, these cloned cultures respectively produced only 9.6 and 28 pg/ml of somatostatin, thereby showing the anticipated lower response to these physiological conditions. Six of 27 clones produced low but significant amounts of insulin, ranging 88.5 to 114 pg/ml/24 hrs. None of the 27 clones made sufficient glucagon to be detected under these culture conditions.

EXAMPLE 6

This example illustrates the preparation of pancreatic endocrine cell strain HPSL-6 and its steady-state production of insulin and C-peptide after various population doublings.

Partially purified islets were prepared from pancreatic tissue collected in St. Louis, using the method described in Example 2. Accordingly, the islets were concentrated by centrifugation, resuspended in Coon's 4506.07 medium and distributed at densities of about 250 islets per standard 100 mmplastic petri plate and fed with twice weekly changes of Coon's 4506.07 medium. The cultures were maintained in water jacketed incubators set at about 36.5° C. and provided with a humidified, 5% $CO_2$ in air gas mixture. Two weeks after initiating the cultures, the cells were trypsinized, and the contents of one plate were distributed into 2 new plates. The cells on these new plates were fed and incubated as before. The cells in these plates reached confluence (i.e., became crowded to the point of becoming contiguous, thereby ending log-phase growth of the culture) in 5 to 7 days, and again the cells from one plate were trypsinized and passaged into 2 more plates (i.e., a 1:2 passage ratio). In this way, the cells may be said to have undergone a doubling or one population doubling in each passage generation. By convention, population doublings (PDL) can be reckoned in this passage-at-confluence method (as done here with HPSL-6) or by counting cells and diluting accordingly at each passage (as done with HPSL-8 in Example 7 below).

At each passage starting with PDL #13 (i.e., after 13 cell divisions or a $2^{13}$-fold (approximately 8000-fold) expansion of the original cell population) and continuing through PDL #18, the production of insulin and C-peptide were determined using standard radioimmunoassay procedures (using RIA kits from Peninsula Laboratories, Inc., Belmont, Calif. 94002). The amount of insulin (striped bars) and C-peptide (blank bars) accumulated in the medium in 24 hours is presented in FIG. 1 (y-axis is hormone production per day, expressed as picograms hormone per 500 ml medium per day; x-axis is population doubling values, expressed as P.D.L.). These are steady state values in the cultures and do not measure the hormone production in response to a glucose stimulus (see Example 7 below). Apparently, after PDL #14 the amount of insulin produced fell off sharply in these cultures, but did not disappear entirely. However, PDL #14 represents an approximately 16,000-fold expansion of the cultured pancreatic endocrine cells, which is ample for the production of thousands of individual grafts that can be derived from a single donated pancreas.

EXAMPLE 7

This example illustrates the preparation of pancreatic endocrine cell strain HPSL-8 and its steady-state production of insulin and C-peptide after various population doublings.

Figure 2:
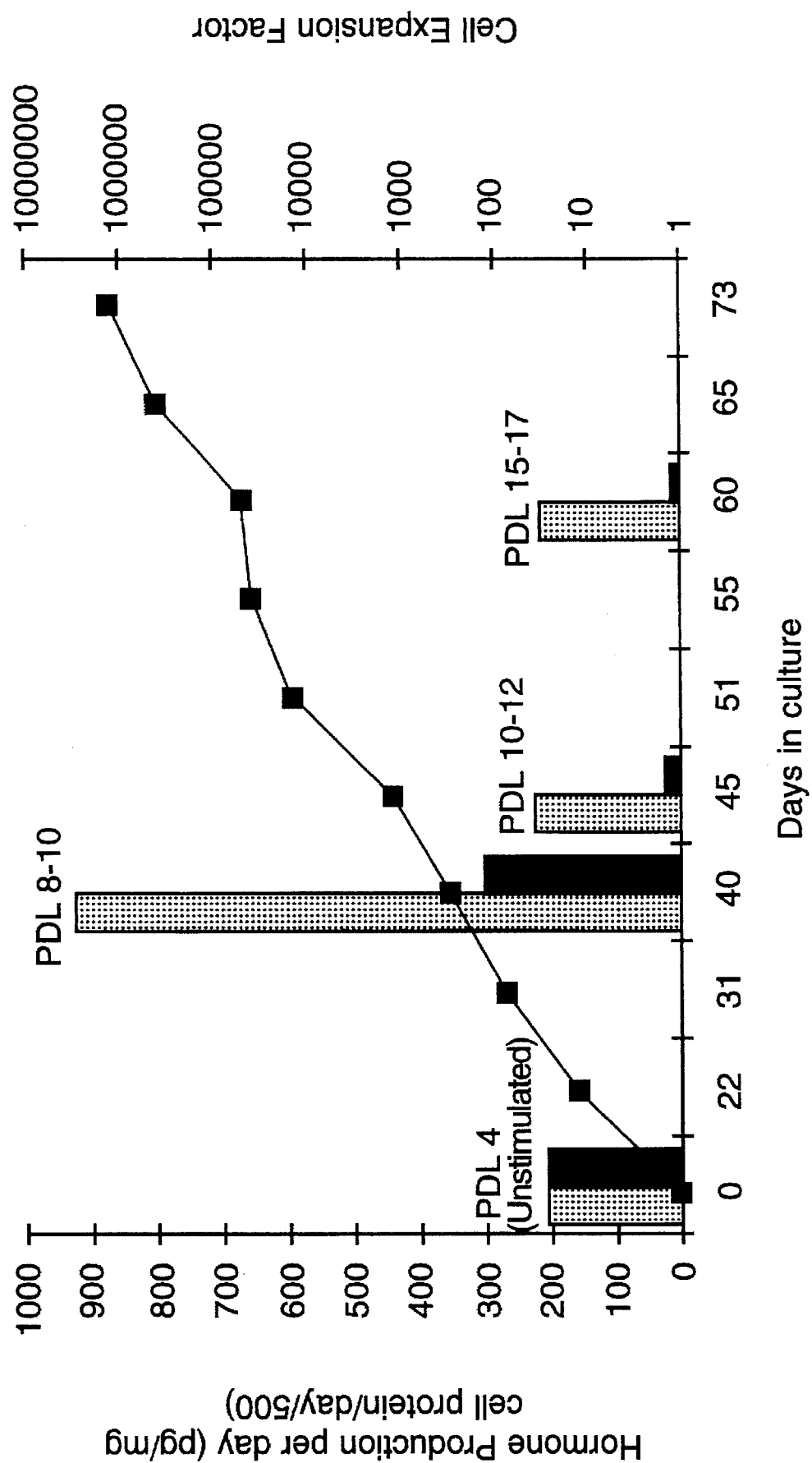
FIG. 2 is a graph that shows the results of glucose stimulation of the HPSL-8 strain of pancreatic cells, in terms of cell growth, production of insulin, and C-peptide.
Figure 3A:
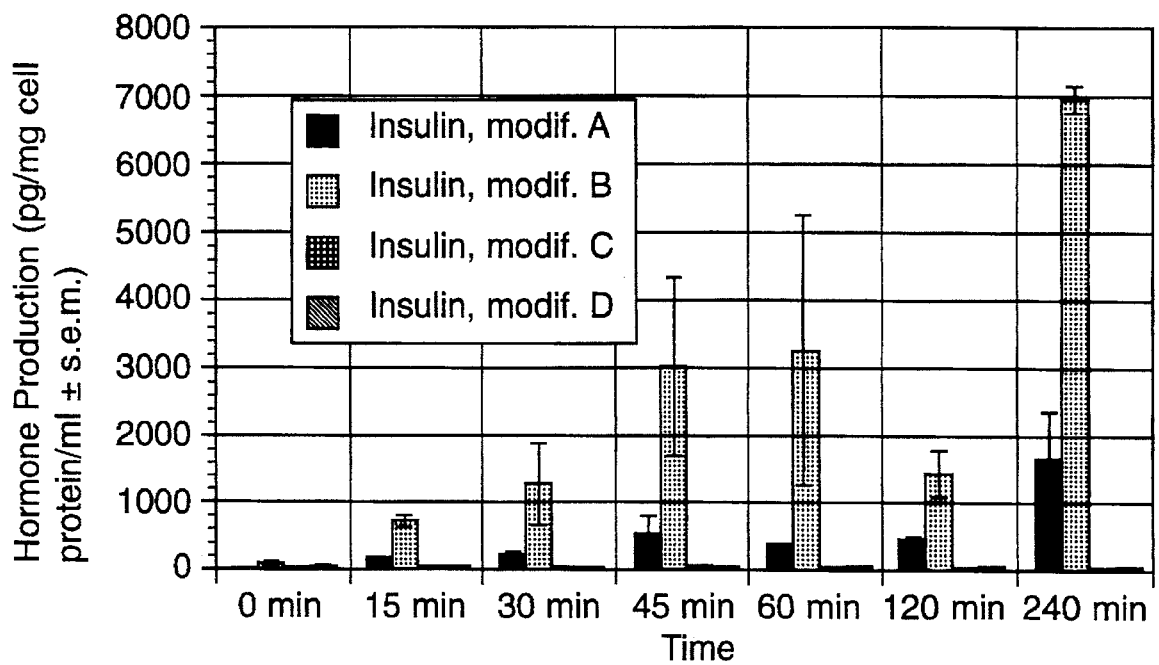
FIGS. 3A–3D are graphs that show the effects of modifications of Coon's 4506.07 medium on hormone secretion by HPSL-8 cells following glucose challenge.
Figure 3B:
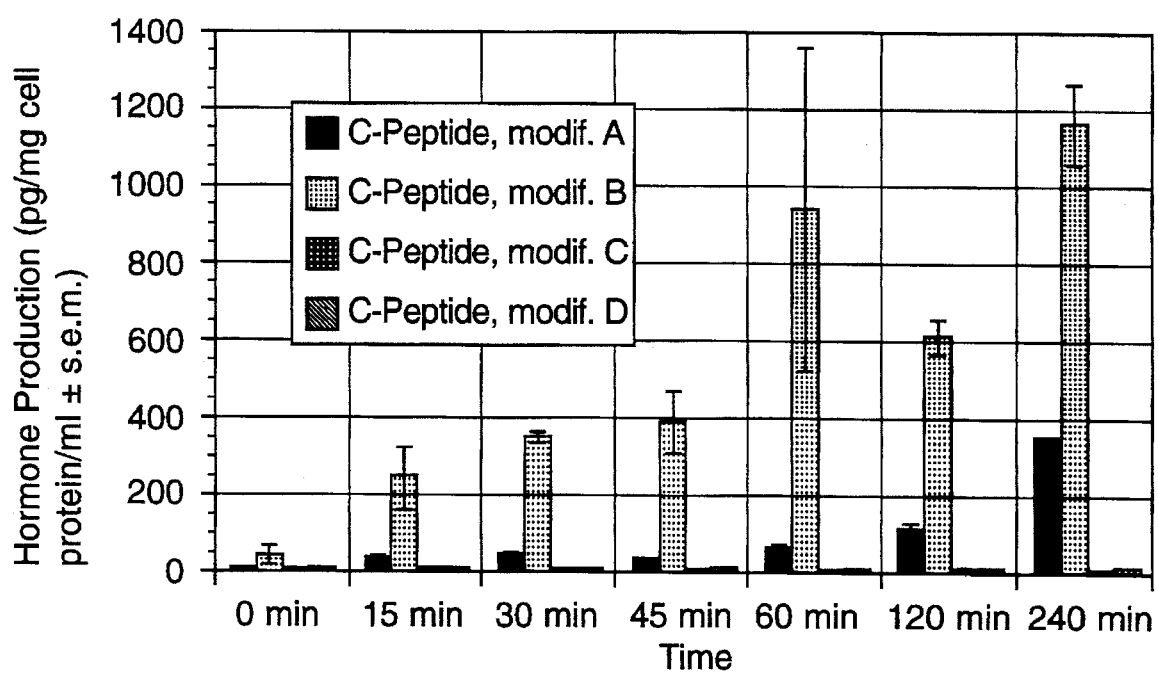
Figure 3C:
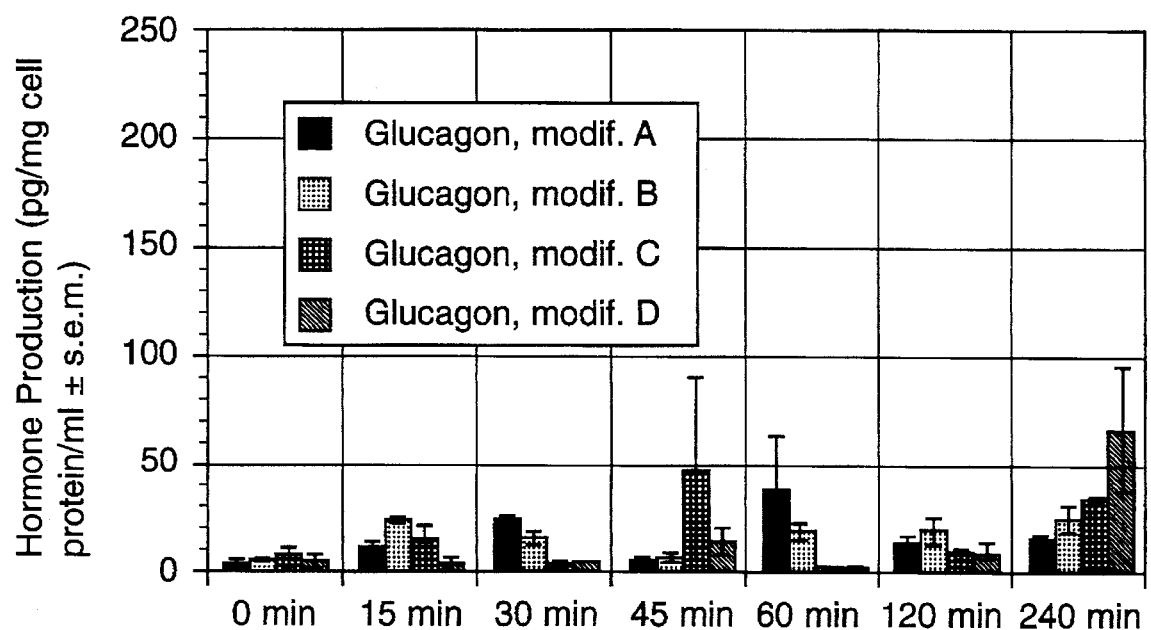
Figure 3D:
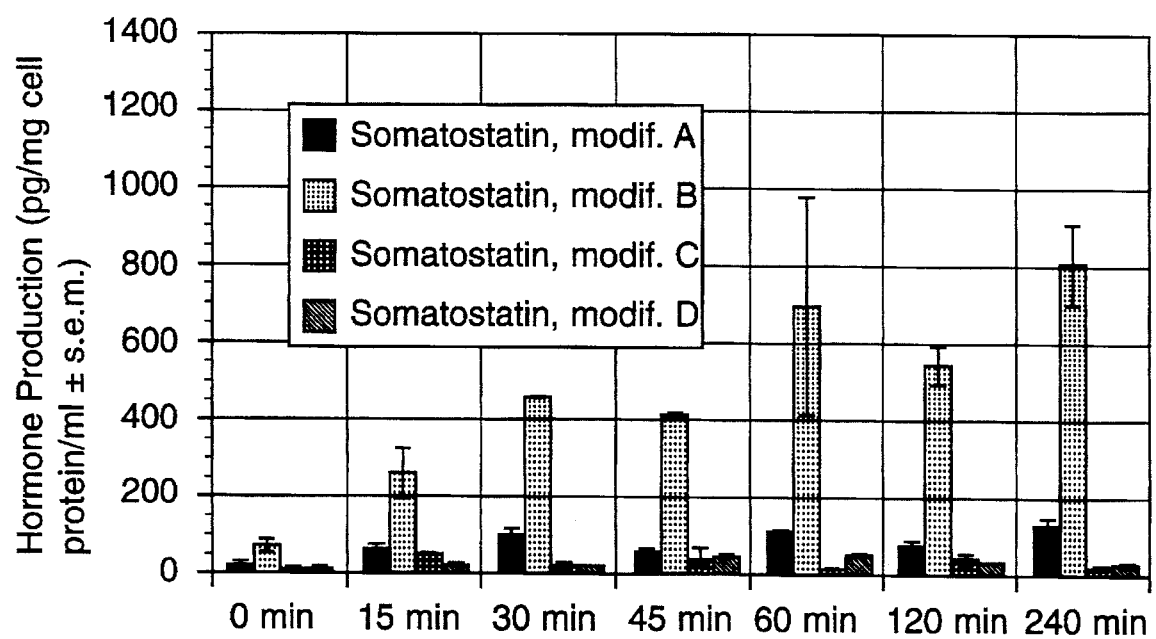
Figure 4A:
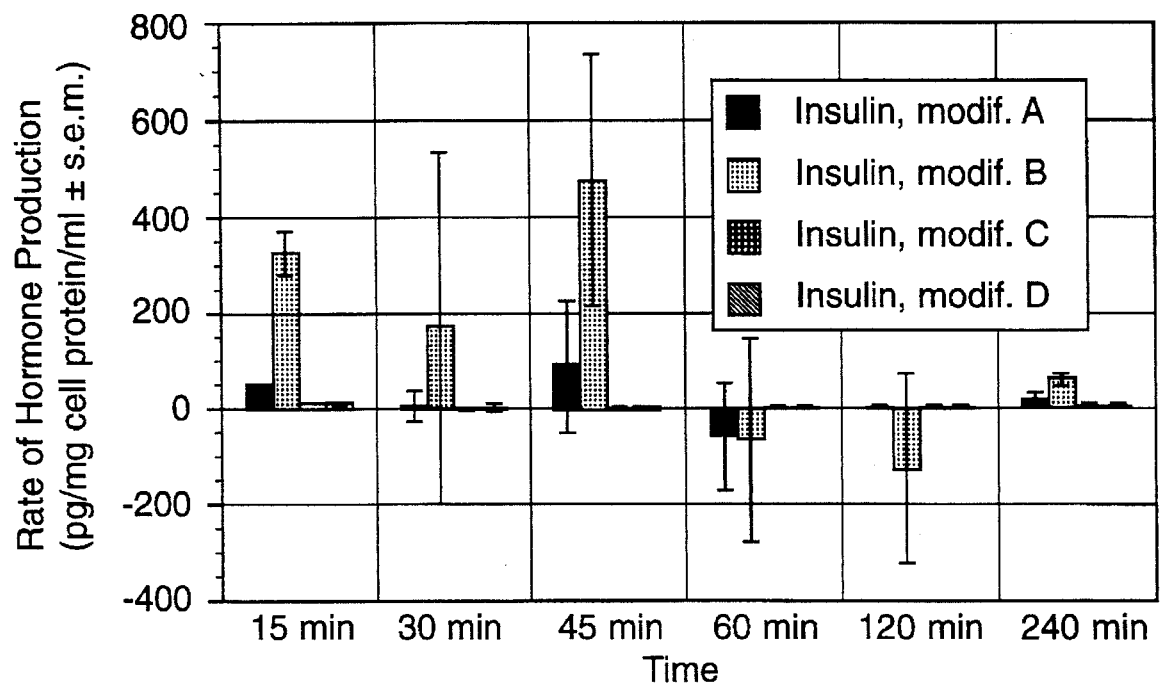
FIGS. 4A–4D are graphs that show the effects of modifications of Coon's 4506.07 medium without added insulin on the rate of hormone secretion by HPSL-8 cells following glucose challenge.
Figure 4B:
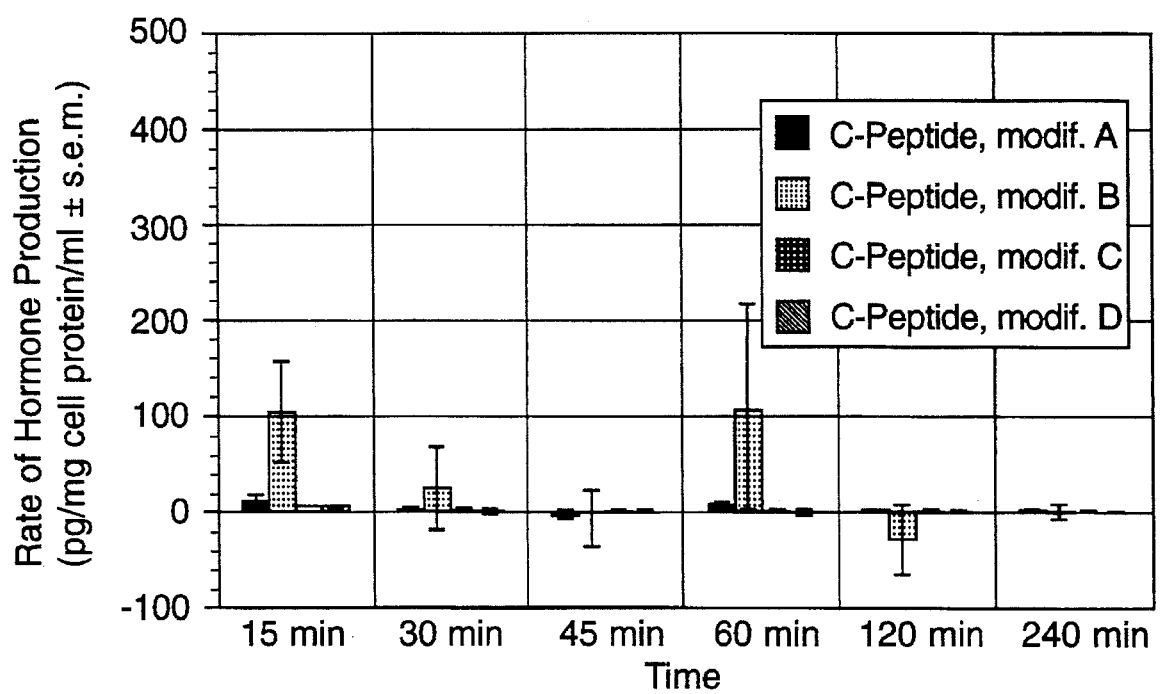
Figure 4C:
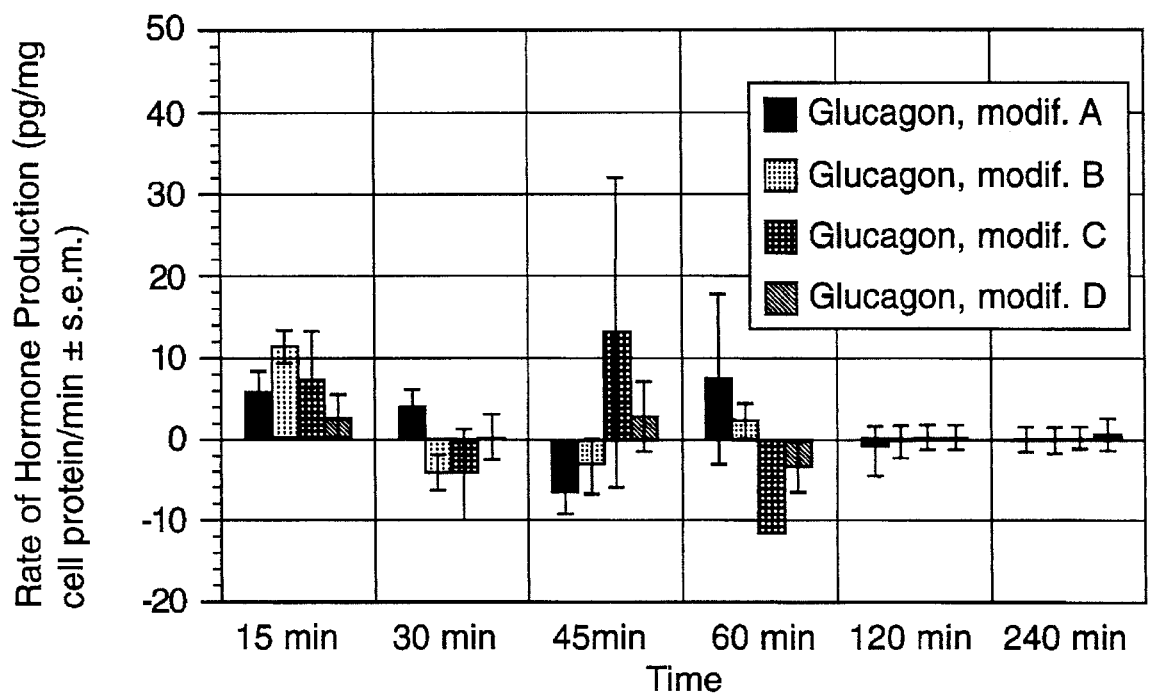
Figure 4D:
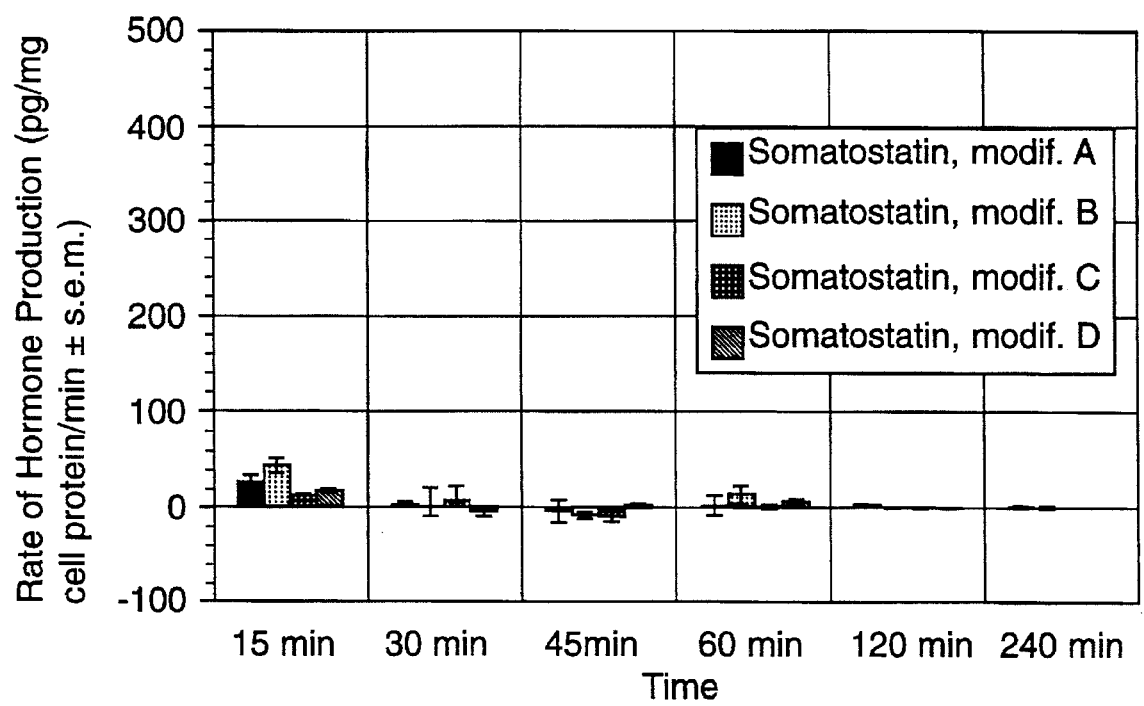

Using the procedures outlined in Example 2 above, another set of partially purified islets, HPSL-8, were grown in serial culture in a manner similar to that set out in Example 6. This time, the initial inoculum was 300 to 500 islets per standard 100 mm diameter petri plate, and the passage ratios were 1:4 for each pass, which occurred approximately every week. Thus, each passage corresponded to two PDL or a quadrupling of cell number. FIG. 2 shows bars that denote the amounts of insulin (stippled bars) and C-peptide (solid bars) produced by cell strain HPSL-8 at various PDL states of the culture. The left y-axis, which is applicable to the depicted bars, has units of pg of hormone per mg of cell protein per day (divided by a scale factor of 500) and the x-axis has units of days in culture. This bar graph is superimposed on the cumulative growth curve (■) for the first 73 days in culture of the cells. The right y-axis, which is applicable to the depicted curve, has units of cumulative number of cells in a logaritharic scale. The values obtained at PDL #2–4 are unstimulated steady state values like those shown for HPSL-6 in FIG. 1. The values obtained at PDL #8–10, #10–12, and #15–17 are calculated from the measured amount of insulin and C-peptide (determined by RIA) produced in a 15 minute period following a change to high glucose (20 mM) medium without added insulin. This measures the ability of cells in the culture to secrete insulin under conditions of high glucose challenge, such as occurs in diabetic individuals.

By PDL #8–10 (about 1000-fold expansion), there were no fibroblasts detected in the expanded cultures, nor were there endothelial cells as judged by the absence of immunofluorescent staining with anti-human-factor-VIII antibodies. Neuron-specific enolase (NSE), a marker for neuroendocrine cells, is seen in all cells of the cultures by immunofluorescent staining. Similarly, another marker, also absent from fibroblasts and endothelial cells, chromogranin A, was demonstrated in all cells of the culture after PDL #8–10. Prior to PDL #8–10, at PDL #2–4 (primaries), there were subsets of cells in the culture that did not stain with these immunochemical reagents.

The population doubling time was about 2.7 days over the 73 days of the study. The amount of insulin produced in response to glucose challenge was found to be about 19 ng per mg cell protein per hour at PDL #8–10. It was also noted that the HPSL-8 monolayer cultures contain glucagon and somatostatin producing cells in addition to the insulin and C-peptide producing cells.

Hormone and C-peptide production in a series of 30 clones prepared from HPSL-8 islets in passage 1 (PDL level 4–6) was assayed using the methods described in Example 5. Insulin was detectable in 6 clones (4 to 6 pg/mg cell protein/ml); no glucagon was found in any clone, and two clones showed high levels of somatostatin (160 and 500 pg/mg cell prot/hr).

EXAMPLE 8

This example illustrates that the HPSL-8 cells and islet or primary culture cells display physiological similarity.

Time course assays using a standard RIA-type assay as in Examples 5, 6, and 7 were performed on culture medium of HPSL-8 cultures for insulin, C-peptide, glucagon, and somatostatin, and the results thereof are shown in FIGS. 3–5. At each time point in these graphs, four modifications of the basic Coon's 4506.07 medium formulation were used, whereby the tested cell culture was incubated in the modified medium for one week prior to the glucose challenge described above. Modification A was low calcium (0.35 mM $CaCl_2.2H_2O$); modification B was low calcium plus 10 µg/ml added human placental lactogen; modification C was high calcium (2.2 mM); and modification D was high calcium plus 10 µg/ml added human placental lactogen. The accumulation over time of insulin, C-peptide, glucagon, and somatostatin are illustrated in Graphs A, B, C, and D, respectively, of FIGS. 3–5. The y-axis is in units of hormone accumulated, namely pg hormone accumulated/mg cell protein/ml±s.e.m.; the x-axis is in units of time, namely minutes.

With respect to the data depicted in FIG. 3, the hormones (or hormone by-product in the case of C-peptide) were secreted into the medium by the cultured HPSL-8 cells, and were measured following a 20 mM glucose challenge in medium without added insulin. From FIG. 3A, it can be seen that the accumulation of insulin secreted into the medium is paralleled after a delay by C-peptide secretion, which indicates active processing of the prohormone to the active hormone. The same data expressed as a rate of insulin secretion over time is presented in FIG. 4. From this profile, a pattern reminiscent of serum insulin values after glucose challenge in an animal can be seen, a rise followed by an undershoot and return to an apparent basal level. The absolute timing is different, but then the stimulation is also different in vitro from that of the in vivo situation because, at a minimum, there is no associated liver to act as a glucose/insulin repository in the culture vessel.

Figure 5A:
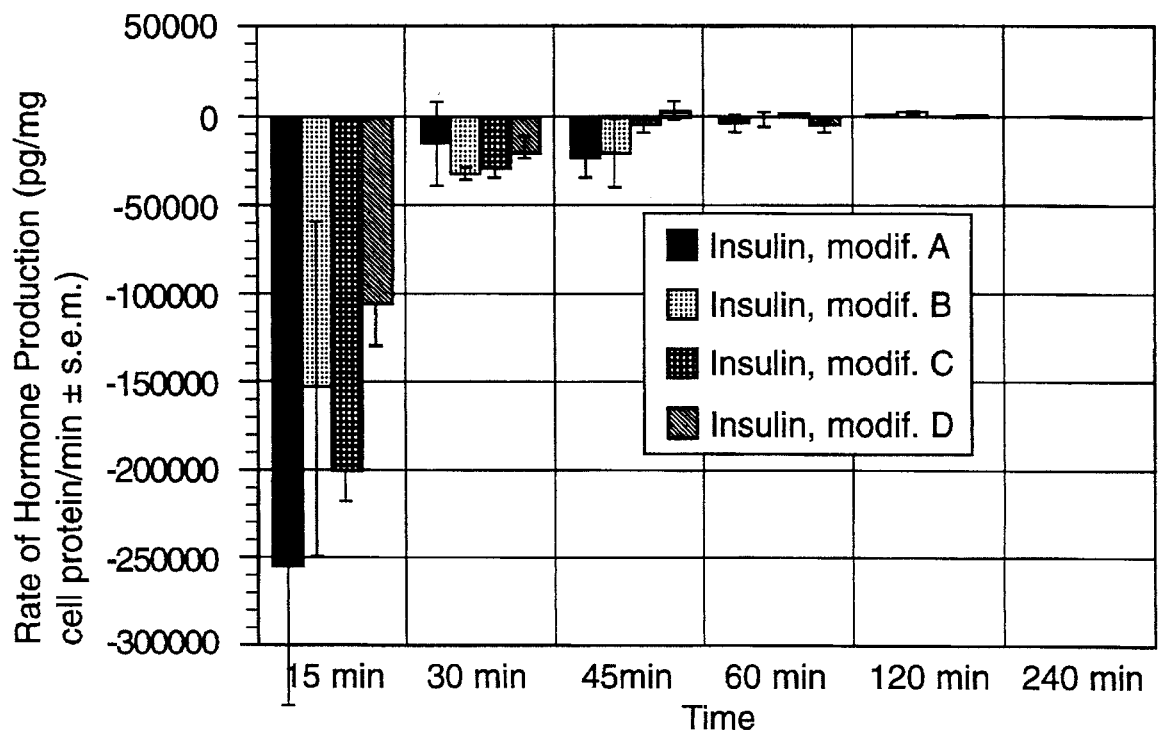
FIGS. 5A–5D are graphs that show the effects of modifications of Coon's 4506.07 medium with added insulin on hormone secretion rate by HPSL-8.
Figure 5B:
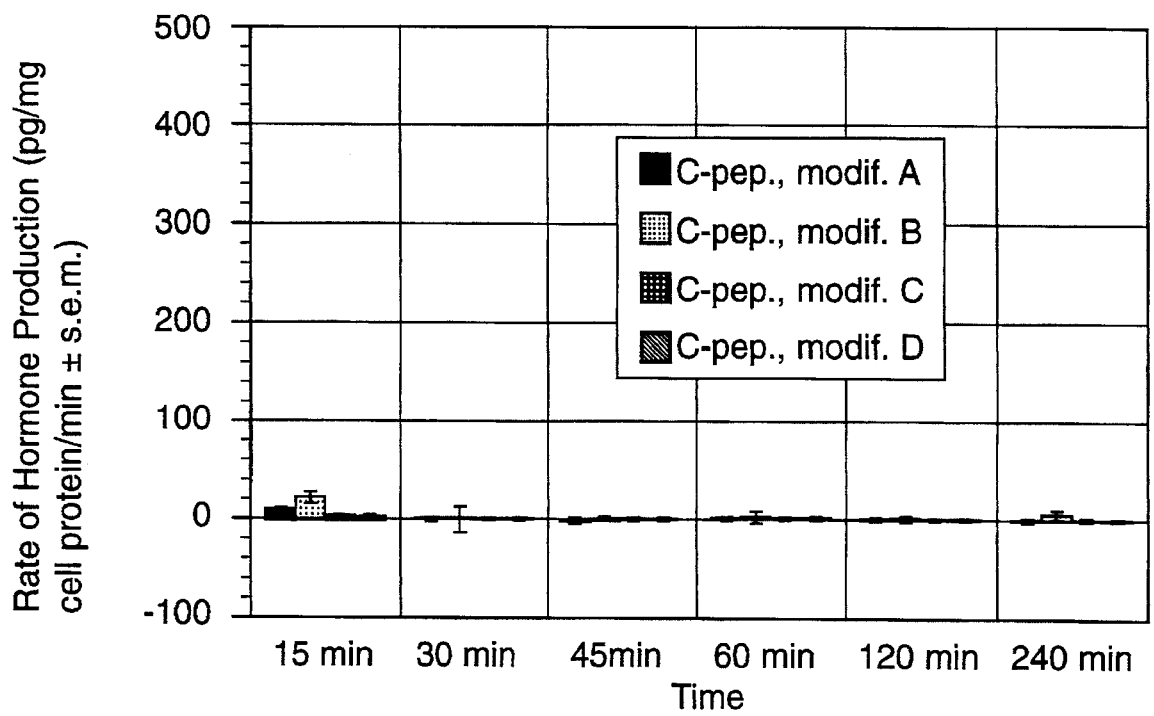
Figure 5C:
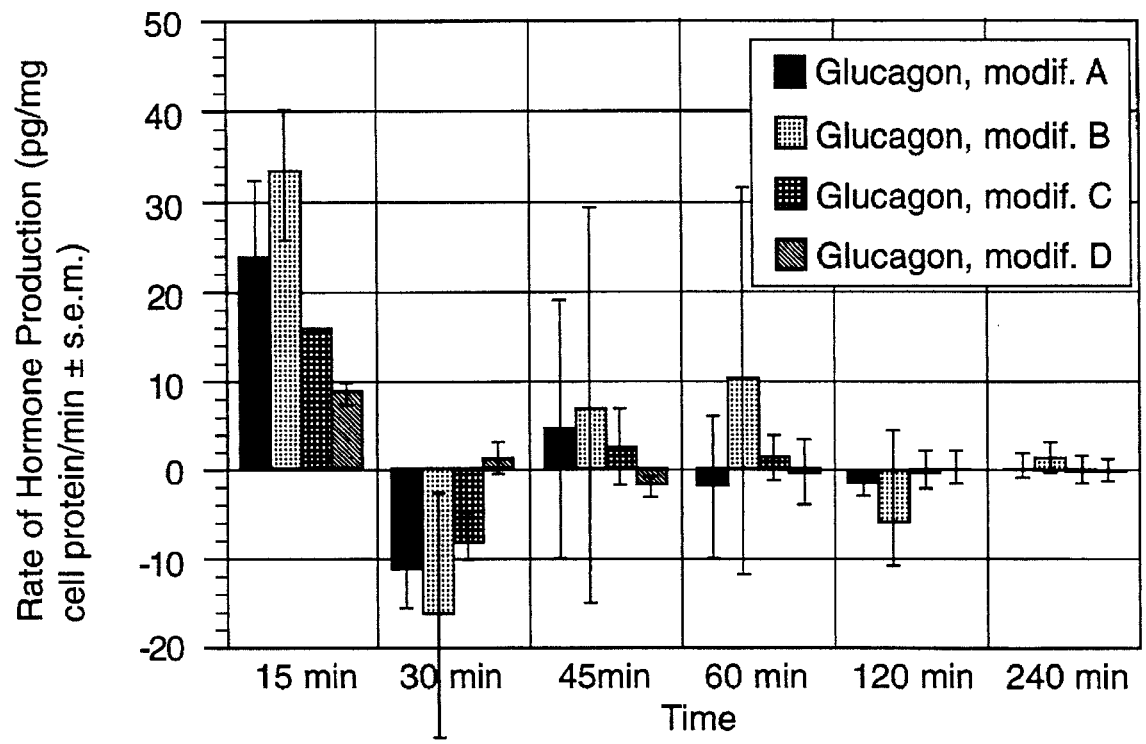

High insulin and low glucose (2.5 mM) stimulate the rate of glucagon secretion, as seen in FIG. 5C. In FIG. 5B, which graphically displays the results of an experiment where the HPSL-8 cells were incubated in high insulin and low glucose, the production of C-peptide is shut off by high levels of insulin in the presence of low levels of glucose. The negative rates of insulin synthesis, shown in FIG. 5A, are interpreted as destruction and ligation and/or uptake of the initial high levels of insulin from the medium.

Figure 5D:
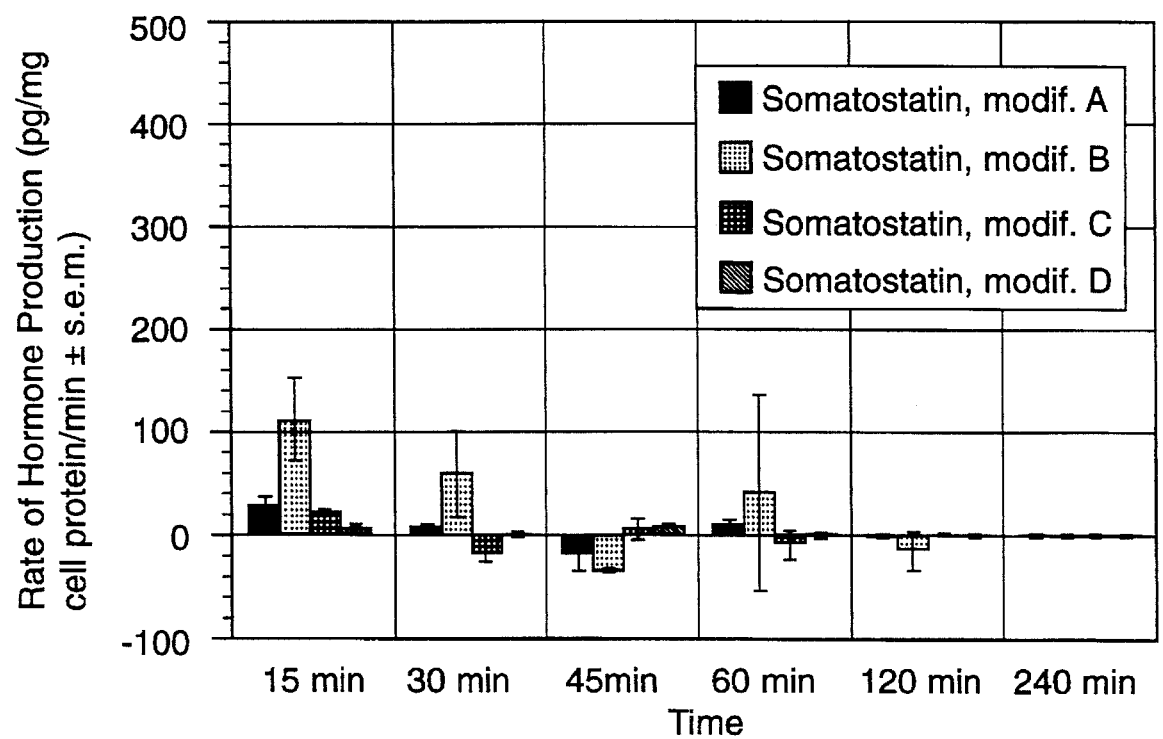

Somatostatin, which is seen at all stages of the cultures, shows variations with differing levels of glucose; it seems to be significantly increased at high insulin and low glucose levels, as shown in FIG. 5D.

In nearly every case, the highest hormone production was observed with the modification B medium. It was particularly notable that high calcium had a negative effect on the generation of insulin by the cultured cells. It was also notable that human placental lactogen, known to enhance insulin secretion by islets and isolated primary cells in Vitro, had the same effect in vitro with the cultured cells. Therefore, the response of the cultured cells to the glucose challenge demonstrated the physiological similarity of these monolayer cell cultures to isolated islets even after an approximately 1000-fold expansion in vitro.

EXAMPLE 9

This example illustrates a method to assay the cytotoxicity of exogenous materials and bodily fluids that uses cultured pancreatic endocrine cells of the present invention. Cytotoxic agents generally, cytotoxic agents specific to pancreatic endocrine cells, and auto-antibodies in individuals having no diabetic clinical symptoms can be assayed using the following procedures.

To measure the stimulatory effect on the basal release of insulin in the presence of serum from diabetic patients or in the presence of some other test material, cells are cultured for 7 days in the presence of either 10% serum from normal individuals (control) or from test subjects, at 8.3 mmol glucose. For non-serum test materials, cells are cultured for 7 days in the presence of either serial dilutions of the test material or the diluent (control). Insulin release is measured in the supernatant medium using standard RIA technology.

To measure the inhibitory effect on the high glucose induced, acute release of insulin in the presence of serum from symptomatic or presymptomatic diabetes patients or in the presence of some other test material, cells are cultured for 7 days in the presence of either 10% serum from normal individuals (control) or from test subjects. For non-serum test materials, cells are cultured for 7 days in the presence of either serial dilutions of the test material or the diluent (control). At the seventh day, cells are challenged with 20 mmol or 5 mmol glucose. Insulin release is measured in the supernatant at 15 minute intervals after challenge to produce a time-course curve.

To measure antibody-dependent cytotoxicity, cultured pancreatic islet cells, prelabeled with sodium [$^{51}$Cr] chromate, are used as targets. In volumes of 50 µl, up to $5\times10^4$ of the labeled target cells, are plated in quadruplicate in a 96 well assay plate. Effector cells (such as human peripheral mononuclear cells) are added in ratios ranging from 100:1 to 12.5:1 (effector:target cells), in the presence of purified immunoglobulins from either normal donors (control) or test subjects. The plates are then incubated for 4 hours at 37° C. Supernatant fluid is harvested and counted in a gamma counter. Specific lysis may be calculated using the following formula:

$$\text{lysis } (\%) = \frac{[\text{observed release (cpm)} - \text{spontaneous release (cpm)}] \times 100}{\text{total release (cpm)} - \text{spontaneous release (cpm)}}$$

where observed release is the mean radioactivity released in the presence of effector cells and sera, and spontaneous release is the mean radioactivity released from target cells incubated in the medium alone. Total releasable activity may be determined after treatment of the target cells with 2.5% Triton X-100.

To measure cellular-dependent cytotoxicity, cultured pancreatic islet cells, prelabeled with sodium [$^{51}$Cr] chromate, are used as targets. In volumes of 100 µl, up to $5\times10^4$ of the labeled target cells, are plated in quadruplicate in a 96 well assay plate. Effector cells (such as human peripheral mononuclear cells or sorted T cells from either normal donors or test subjects) are added thereto in ratios ranging from 100:1 to 12.5:1 (effector:target cells). MHC class I restricted activity is excluded by testing the cells either with class I matched or nonmatched cultures or in the presence and in the absence of anti-class I blocking antibodies. The plates are then incubated for 4 hours at 37° C. Supernatant fluid is harvested and counted in a gamma counter. Specific lysis may be calculated using the following formula:

$$\text{lysis } (\%) = \frac{[\text{observed release (cpm/min)} - \text{autologous release (cpm/min)}] \times 100}{\text{total release (cpm/min)}}$$

where observed release is the mean radioactivity released in the presence of effector cells, autologous release is the mean radioactivity released by target cells incubated with $2\times10^5$ unlabeled autologous cells in place of effector cells, and total releasable activity is the total amount of radioactivity incorporated in target cells.

EXAMPLE 10

This example illustrates a method for altering blood sugar levels in a mammal in need of altering its blood sugar levels that uses cultured pancreatic endocrine cells of the present invention.

Late passage cultivated islet cells of the present invention as coherent aggregates of cells (pseudoislets) or suspended cells were incubated in animal collagenous matrix that was caused to gel, thereby forming pseudotissues suitable for grafting into a host animal. In particular, HPSL-8 cells of PDL #19–21 were suspended in an isotonic neutral collagen solution which was allowed to gel at 37° C. for three hours, thereby forming cell-type pseudotissues composed of about $6.5\times10^6$ total cells each. HPSL-8 cells of PDL #23 also were reaggregated spontaneously by gentle rotation of suspended cells in an Erlenmeyer flask at 37° C. for three days. During these three days, the cells reaggregated into groups of from about 20 to about 250 cells, forming pseudoislets of tightly adherent islet-like spherical masses. These masses were further embedded in a collagen gel as above, resulting in pseudoislet-type pseudotissues.

Figure 6A:
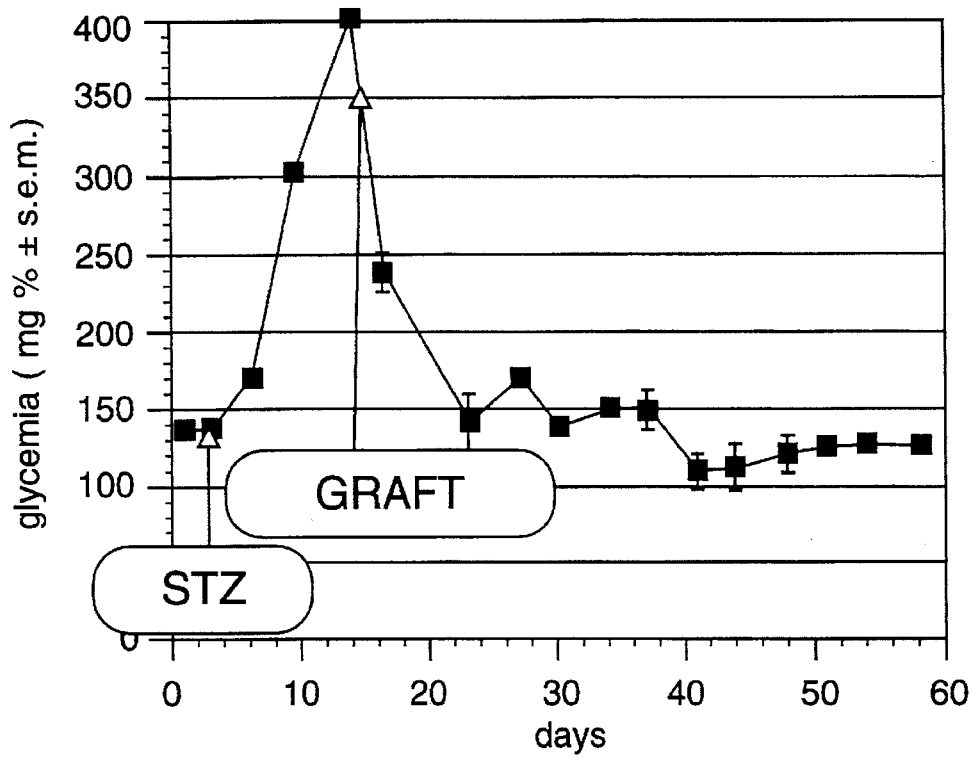
FIGS. 6A–6B are graphs that show the regulation of blood sugar levels in diabetic mice that have received grafts of pseudotissues comprising of pseudoislets or suspended cells.
Figure 6B:
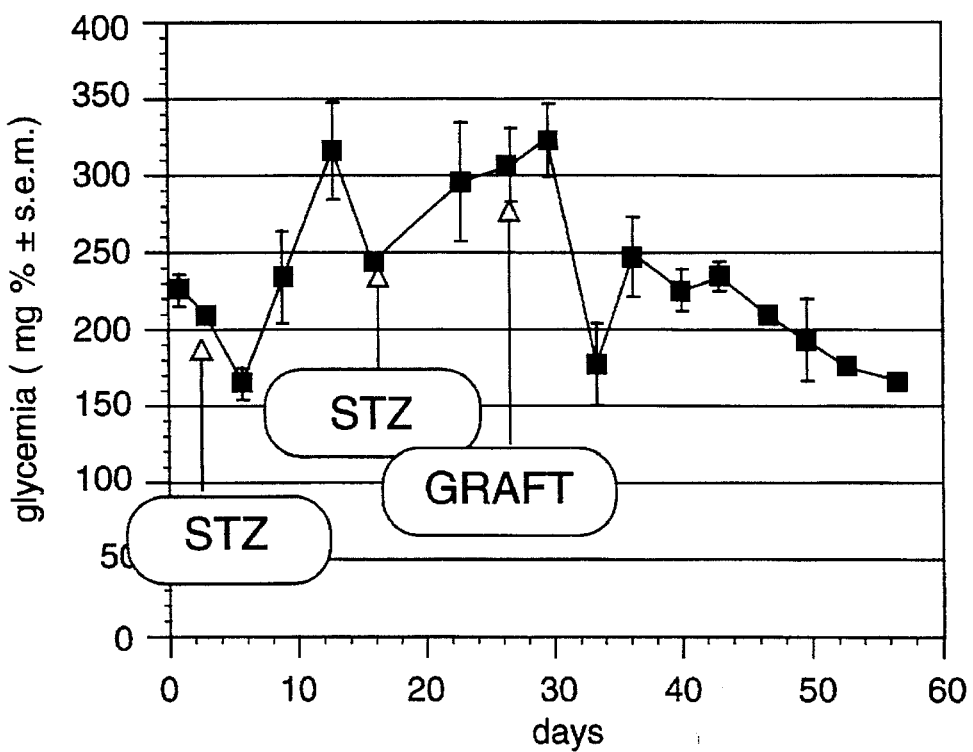

Severe combined immune deficiency (SCID) mice that were homozygous at the SCID locus and whose blood sugar was assayed over a period of up to 58 days were used to demonstrate that the above-described pseudotissues work in vivo to restore normoglycemia, as shown in FIG. 6 (wherein the y-axis unit is mg %±s.e.m. for measurement of glycemia, and the x-axis unit is days). Blood sugar determinations were made (approximately) twice weekly using the Ames Glucostix and the Ames Glucometer II on a drop of blood from a cut in the tail vein of each mouse. First, the subject mice were caused to be diabetic by administering to each mouse a freshly dissolved solution of streptozoticin ("STZ" in FIG. 6), an established procedure for experimentally causing a mouse to be diabetic by preferentially killing the insulin-producing pancreatic beta cells. The animals were observed for about two weeks to ensure that their blood sugar levels rose to the diabetic range, which is taken to be greater than 300 mg per 100 ml. The mice were then supplied with a subcutaneous graft of human pancreatic culture cells of the present invention (HPSL-8 at PDL #19–21) in the region of the dorsal fat pad (between the shoulder blades).

The result with host mouse 24S (FIG. 6A), using a graft of cultured human islet cells bound into a cell-type pseudotissue, is a clear example of a successful graft of greatly expanded human islet cells. The blood sugar became regulated down to normal levels very rapidly and remained there for at least three weeks, the duration of the experiment. Host mouse 20S, which received a graft of a pseudoislet-type pseudotissue, appears to have received a successful graft as well, although not as profoundly so (see FIG. 6B). This mouse required an extra administration of the streptozotocin to induce its diabetic condition. Nevertheless, over the course of the experiment, it is clear that blood sugar levels were regulated after the implant of the graft of the pseudotissue.

Post mortem examination of the pancreas of host mouse 24S showed that very few beta cells survived, as anticipated. This examination occurred 56 days after the streptozotocin treatments. Standard histological techniques were used, namely immunohistochemical staining for insulin of histological sections of the host mouse's pancreas. In the graft (located beneath the skin by a marker of blue tatoo ink included at the time of grafting), it was possible to see human cells that were heavily stained for insulin and were clustered around capillaries that had invaded the grafted tissue. It is known that human beta cells apply themselves directly to islet capillaries, whereas in mouse and pig islets, the beta cells are usually one or two cell layers removed from the capillaries. Human cells were unequivocally identified by indirect immunofluorescence using monoclonal antisera directed against human class I histocompatibility antigens. These observations demonstrate clearly that the human cells of the graft were able to establish abundant insulin synthesis and storage and to organize themselves characteristically with respect to the capillaries even after an approximately 1,000,000-fold expansion in cell culture. The human cells of the graft apparently were instrumental in restoring the normoglycemia observed in the mouse immediately after grafting.

EXAMPLE 11

This example illustrates methods to culture and clone normal human thyroid cells according to the present invention.

Coon's 4506.035 or Coon's 4506.07 medium was prepared as in Example 1, except that the concentration of $MgCl_2$ was adjusted to 0.48 mM, the concentration of hydrocortisone was adjusted to 0.01 mM, the concentration of selenous acid was adjusted to 2 ng/ml, the triiodothyronine concentration was adjusted to 3 pg/ml, bovine hypothalamus extract was added to a final concentration of 75 µg/ml, and bovine pituitary extract was added to a final concentration of 5 µg/ml.

All preparation and treatment of thyroid tissue was performed under sterile conditions, similar to the procedures used for rat cells reported in Ambesi-Impiombato et al., Proc. Natl. Acad. Sci. USA, 77:3455–3459 (1980). Normal human thyroid tissue, obtained from an organ donor, was freed of thyroid tissue attached thereto from adherent connective tissue, cut into small (less than 1 mm diameter) pieces, washed in $Ca^{++}$- and $Mg^{++}$-free Hanks' balanced salt solution (HBSS) by a 5 minute centrifugation at 500×g, and dissociated enzymatically. The enzymatic digestion was performed according to the method of Coon, Proc. Natl. Acad. Sci. USA, 55:66–73 (1966), for which a solution is prepared consisting of 20 U/ml collagenase, CLSPA (Worthington, Freehold, N.J.), 0.75 mg/ml trypsin, 1:300 and 2% heat-inactivated dialyzed chicken serum (Gibco) in $Ca^{++}$- and $Mg^{++}$-free HBSS (hereinafter referred to as "CTC solution"). The digestion was done in a shaking water bath at 37° C for two hours, after which the tissue was mostly a cell suspension. Larger fragments were allowed to settle for 2 minutes at 1×g. Supernatants were collected, and then cells and small fragments of follicles were seeded at a density of $10^5$ cells per 100 mm plastic tissue culture dish (Falcon, Becton Dickinson, Lincoln Park, N.J.).

Secondary cultures were made by incubating monolayers in CTC solution for about 25 minutes at 37° C., after washing in $Ca^{++}$- and $Mg^{++}$-free HBSS. For cloning, single cell suspensions were plated at $10^2$–$10^4$ cells per 100 mm dish. Cloning plates were fed with medium conditioned by preincubating 12 ml of fresh medium for 24 hours in crowded plates of the "parental" mass cell populations. Individual, well-isolated epithelial colonies arisen from previously marked single cells were trypsinized selectively using cloning cylinders.

These culture procedures and media yielded proliferating thyroid cell cultures from different human donors. Neither the presence of 6% FCS, the pituitary extract alone, nor the hypothalamus extract alone were sufficient to sustain the growth of human thyroid cells. In the presence of serum, without any extract or with either one of them, cells were unable to divide (at least not appreciably), and the cytoplasm became swollen and very pale. Each culture showed noticeable differences in the requirements for pituitary extract, as compared to pancreatic islet cells. In most instances, 50 µg/ml of pituitary extract was evidently in excess. As observed under phase-contrast microscopy, cells became gradually larger, contained evident stress-fibers, and ultimately died. Pituitary extracts added to a concentration of 5 µg/ml or less supported healthy-appearing cultures.

EXAMPLE 12

This example illustrates assays used to characterize the thyroid cell cultures of the present invention, and provides results of such assays and general observations that relate to the HNTB-2K clonal cell strain.

Thyroglobulin (Tg) production was determined in the supernatants by a standard immunoradiometric assay method using a commercial kit (Henning, Berlin, Germany) according to manufacturer's instructions.

For chromosomal counts, 2 hours after medium changing, cells were treated with 10 µg/ml demecolcine (Colcemid, Calbiochem, La Jolla, Calif.) for 3 hours, released by enzymatic treatment with CTC solution as disclosed in Example 11, centrifuged, and resuspended in hypotonic solution (4 parts of 5.6 gr/l KCl and 1 part of 7.3 gr/l $CaCl_2 \cdot 2H_2O$). After 15 minutes, cells were fixed by progressively adding 0.1 ml, 0.2 ml and 0.5 ml of fixative (methanol/acetic acid, 3:1, vol/vol) to the cell suspension, followed by 5 minutes centrifugation at 1000×g and pouring off or aspirating the supernatant. Up to 5 ml fresh fixative was then added, dropwise under gentle shaking, followed by centrifugation and elimination of the supernatant, as above. Three more fixing cycles were performed by repeating the above procedure. Fixed cells were then spread on microscope slides, and 25 metaphase-staged cells were observed using phase contrast optics and a drawing attachment.

The ability of TSH, alone or in the presence of insulin, to stimulate cell growth was tested by 3H-thymidine incorporation. TSH-induced 3H-thymidine incorporation was assayed as described in *FRTL5 Today—proceedings Of The First International Workshop On Characterization And Standardization Of An In Vitro Thyroid Cell System*, (Ambesi-Impiombato and Perrild, eds., Elsevier Science Publishers, 1989) (hereinafter "FRTL5 Today") with minor modifications, as follows: Normal human thyroid cells (HNTB-2K) and cultured rat thyroid cells (FRTL5) were seeded in 24 multiwell plates at densities of $5 \times 10^4$ and $4 \times 10^5$ cells/well, respectively, in complete medium. After 24 hours, the cells were washed three times in $Ca^{++}$- and $Mg^{++}$-free HBSS and then shifted to 0.5% FCS, extract-free medium, with no added TSH. After 7–14 days, cells were washed twice in $Ca^{++}$- and $Mg^{++}$-free HBSS and incubated 72 hours at 37° C. in 0.5 ml/well of medium with no thymidine, containing 0.1% bovine serum albumin (BSA) (Janssen, Olen, Belgium), 2.5 μCi/ml 3H-thymidine (Amersham, Arlington Heights, Ill.), no insulin or 4 μg/ml insulin, no TSH or bovine TSH (Sigma), at concentrations varying from $10^{-7}$M to $10^{-13}$M. At the end of incubation, cells were washed twice in $Ca^{++}$- and $Mg^{++}$-free HBSS and twice with 0.5 ml/well of ice-cold 10% trichloracetic acid. After removal of supernatants, 0.5 ml/well of 2% sodium dodecyl sulfate was added, and 10 minutes later supernatants were analyzed for incorporated 3H-thymidine by liquid scintillation spectroscopy.

TSH-induced cAMP accumulation was assayed as described in *FRTL5 Today* with minor modifications, as follows: HNTB-2K and FRTL5 cells were seeded in complete medium at densities of $5 \times 10^4$ and $2 \times 10^5$ cells/well, respectively, in 96 multiwell plates. After incubation for 24 hours, the cells were washed three times in $Ca^{2+}$- and $M^{2+}$-free HBSS and then shifted to 0.5% FCS extract-free medium, with no added TSH. After 7–14 days, cells were washed twice in Krebs-Ringer buffer and incubated 1 hour at 37° C. in 0.1 ml/well of the same buffer, with 0.1% BSA (Janssen), 2 mg/ml glucose, 0.5 mM 3-isobutyl-1-methylxanthine, and bovine TSH (Sigma) at concentrations varying from $10^{-7}$ to $10^{-13}$ M. The reaction was stopped by removing the incubation medium and adding 0.1 ml/well of ethanol. After 20 minutes at room temperature, plates were centrifuged, supernatants were transferred to plastic tubes, and the ethanol was evaporated at 40° C. The quantity of cAMP was determined by a commercial radioimmunoassay kit (Diagnostic Products Corporation, Los Angeles, Calif.) according to manufacturer's instructions.

The following chart lists thyroglobulin production by different clones of thyroid cells derived from normal human donors:

| Cell Line | PDL | TG (ng/cell/day) |
| --- | --- | --- |
| HNTB-1 | 20 | 1317 |
| HNTB-1 CL A | 20 | 18 |
| HNTB-1 CL D | 20 | 25 |
| HNTB-1 CL F | 20 | 21 |
| HNTB-1 CL G | 18 | 22 |
| HNTB-1 CL G | 20 | 28 |
| HNTB-1 CL K | 15 | 92 |
| HNTB-1 CL J | 20 | 19 |
| HNTB-2 | 18 | 1267 |
| HNTB-2 CL A | 15 | 28 |
| HNTB-2 CL B | 15 | 46 |
| HNTB-2 CL C | 15 | 77 |
| HNTB-2 CL E | 15 | 18 |
| HNTB-2 CL F | 15 | 44 |
| HNTB-2 CL H | 15 | 18 |
| HNTB-2 CL I | 15 | 20 |
| HNTB-2 CL K | 15 | 1234 |
| HBTB-2-CL K | 20 | 1262 |
| HNTB-2 CL J | 15 | 22 |

The clone morphology of HNTB-2K was not homogeneous when observed in phase-contrast microscopy, and was influenced by the proliferative state of the cells: non-confluent, log-phase cultures showed mostly elongated, rather pale cells, while at confluence they became more like classical epithelia, showing darker cytoplasm and many secretory granules inside. The karyotype showed a normal diploid number of chromosomes in all metaphases counted. In the complete medium, the population doubling time of the cells of the HNTB-2K clone was 58 hours.

Figure 7:
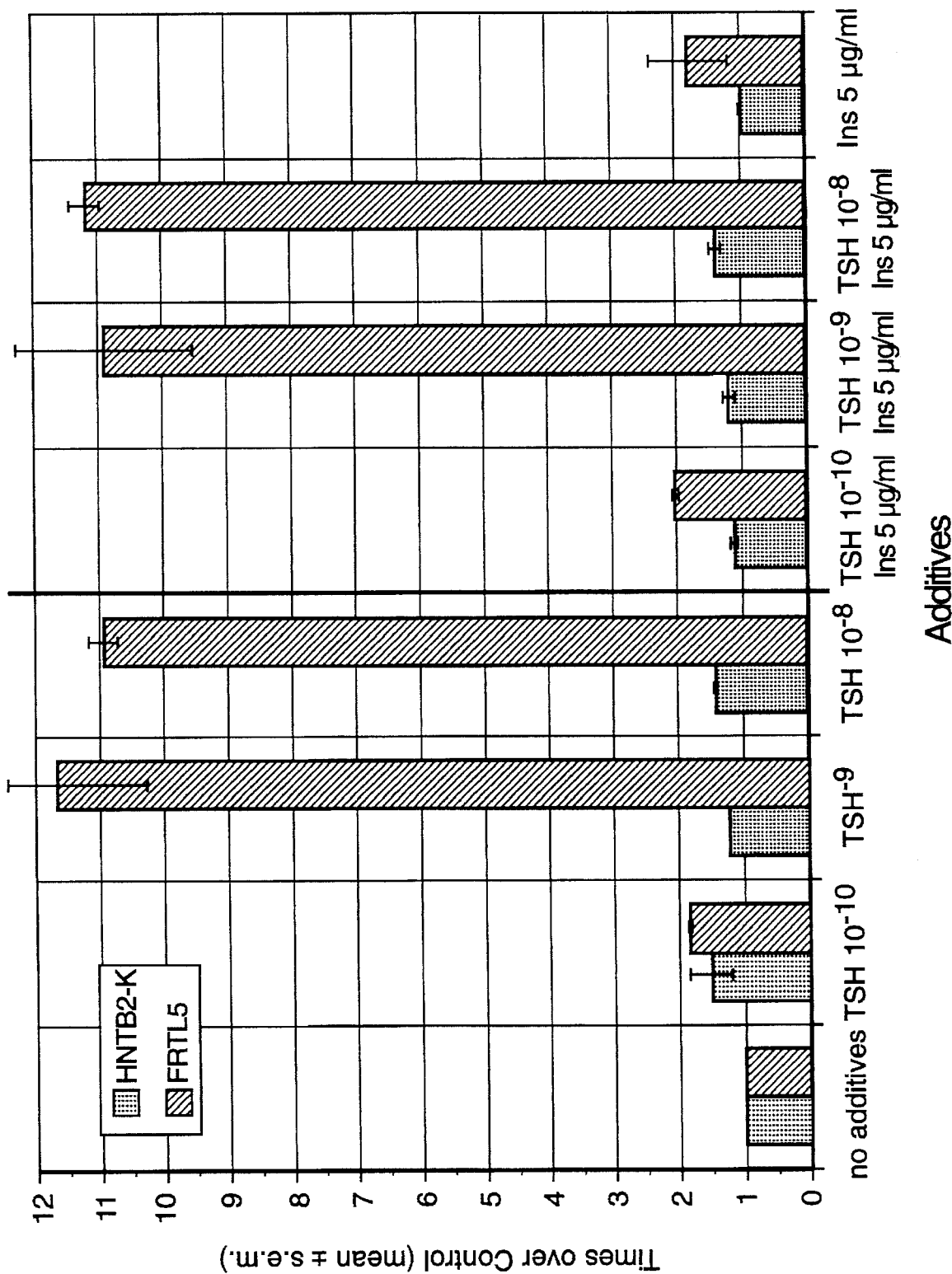
FIG. 7 is a graph that shows the effect of TSH with and without insulin on the growth of thyroid culture cells.

At all concentrations tested, TSH, alone or in the presence of insulin, was unable to stimulate acutely $^3$H-thymidine incorporation, in contrast to the rat system (FRTL5) where TSH is reportedly a mitogenic factor. FIG. 7 shows the acutely stimulated $^3$H-thymidine incorporation by FRTL5 (control; cross-hatched bars) and the lack of response by HNTB-2K (stippled bars) cells in the presence of TSH at various concentrations, alone and with insulin at a concentration of 5 μg/ml. Values are expressed as tissues over control.

Figure 8:
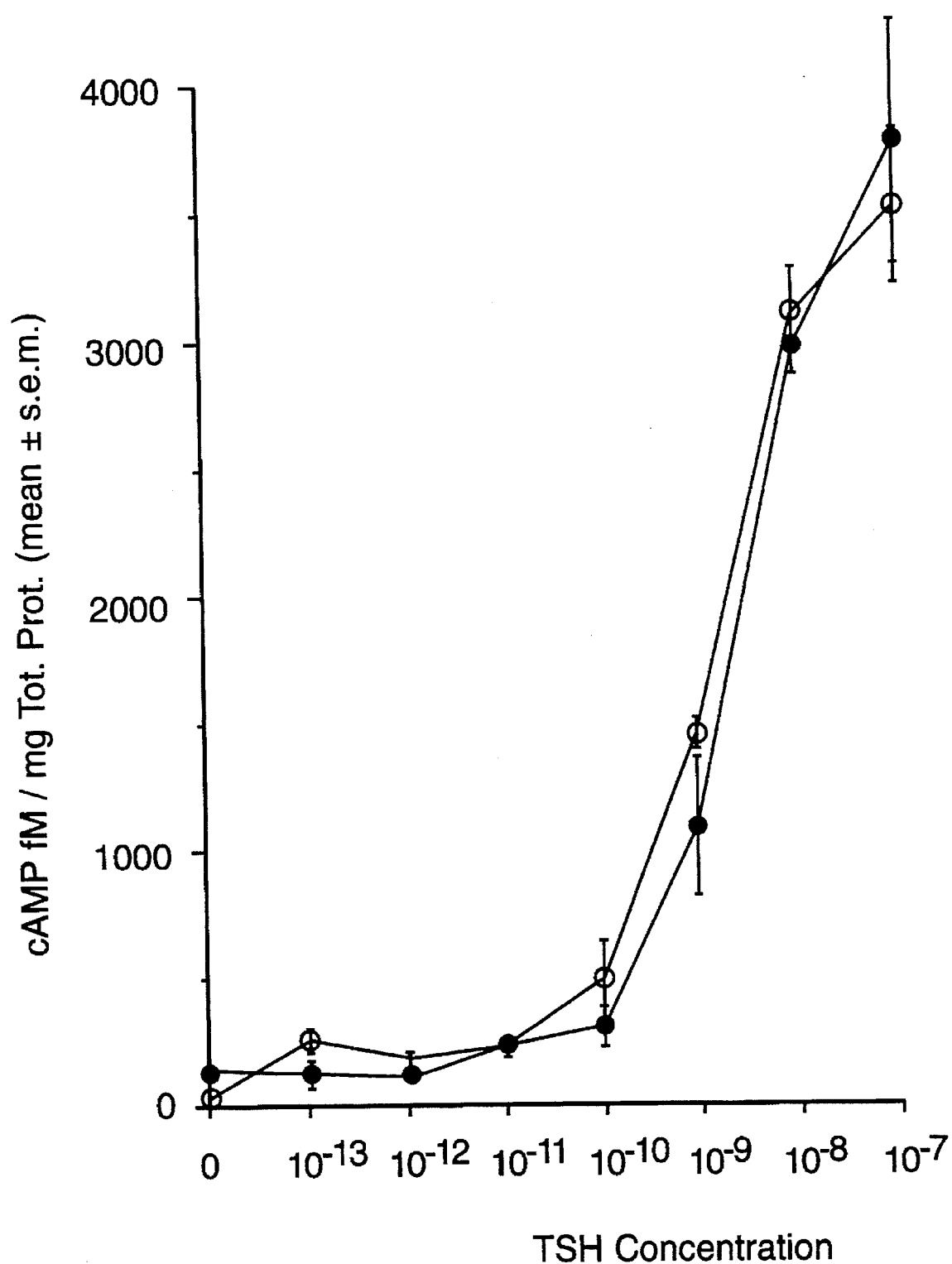
FIG. 8 is a graph that shows the TSH-stimulated dose-dependent increase of cAMP accumulation in FRTL or NHTB-2K cells.

Acutely added TSH was able to induce a dose-dependent, up to 10-fold increase, of cAMP accumulation in HNTB-2K cells. The stimulation was evident, within 1 hour, even at very low concentrations ($10^{-11}$M). The behavior of HNTB-2K cells in this assay is remarkably similar to that of rat thyroid cells in the same assay. FIG. 8 shows the TSH-stimulated dose-dependent increase of cAMP accumulation in FRTL5 (control; closed circles) or HNTB-2K (open circles) cells. Cells that received various concentrations of TSH were assayed for concentration of cAMP per mg total protein, as indicated on the y-axis of FIG. 8.

The HNTB-2K cells appear not to be transformed because they do not exhibit any of the usual symptoms of transformed cells: (1) they do not grow in soft agar; (2) they have retained a diploid karyotype; (3) they have shown no decrease in serum or extract requirement for growth; (4) as part of another experiment HNTB-2K did not make tumors in 45 days after two SCID mice received grafts of $5 \times 10^6$ and $10^7$ cells; and (5) the cloning efficiency has not increased with successive generations in culture.

EXAMPLE 13

This example illustrates the culturing of parotid cells in accordance with the present invention.

Culture medium was prepared according to Example 1. Two organ donated samples ($\leq 2$ gm) of normal parotid gland and 2 surgical samples from normal appearing portions of the parotid gland were removed when the whole gland was resected for cancer therapy. In all four samples of the apparently healthy parotid gland from different adult humans, parotid cells were cultured successfully. The tissue samples were put into culture within 3 hours after removal from the patients.

In each case, the method of transferring the cells to culture was substantially the same. One to two grams of healthy tissue were dissected and minced by repeated snips of blunt tipped "iris" scissors at the edge of a tilted petri dish. When the tissue was reduced to 1–2 $mm^3$ bits, a trypsin-collagenase digestion mixture was added (2–4 ml), and the tissue was incubated for 1–4 hours at 37° C. and also for 12–15 hours (overnight) at room temperature (21° C.). During this digestion the tissue was reduced to single cells and small pieces of the glandular tissue consisting of 50–100 cells. After vigorous mixing to break up the clusters further, the cells were washed in fresh medium (Coon's 4506.07). Cells and fragments were plated in from 3–10 100 mmplastic tissue culture petri plates and cultured in 12 ml of Coon's 4506.07 medium for 7–10 days in humidified, 5% $CO_2$ atmosphere incubator at 36.5° C.

An alternative method for the very small amounts of tissue that are derived from a needle biopsy has been used, whereby the salivary gland cells and minced pieces (about 1 $mm^3$) were embedded in a gel made from reconstituted basement membrane according to Kleinman et al., *Biochemistry*, 25:312 (1986). Reconstituted basement membranes are composed of an extract of EHS mouse chondrosarcoma tumors, which consist largely of type IV collagen. This extract of extracellular material, with a biochemical composition similar to that of normal basement membrane or lamella, was shown by Kleinman et al. supra, to promote the growth and differentiation of a wide variety of epithelial cells, and is available commercially from Collaborative Biomedical, a division of Becton Dickinson, Lincoln Park, N.J., as "Matrigel™".

In either primary culture situation, the salivary cells grow out in about a week or two, at which time they are treated with trypsin and collagenase, washed, and diluted into new, secondary cultures (designated passage 1 or P1). After the cells have spread out on the surface of the plate or under and within the meshes of the reconstituted basement membrane gel, they may be released with minimal cell damage, using trypsin and collagenase and then inoculated into fresh plates at split ratios of from 2–10 to 1 or diluted and plated at 500, 1000, 2500, 5000 cells/100 mm plate for cloning. Plating efficiencies varied with the donor from a low value of 0.01% to a high value of 0.1%. After two to three weeks of culture in homologously conditioned medium (CM), colonies were isolated, grown into populations (clonal cell strains) that were routinely fed twice weekly with a complete exchange of fresh medium 4506.07. Aliquots of these populations were frozen for archival storage and the remaining cells were assayed for salivary glycoproteins: gustin and lumicarmine using indirect immunocytochemistry (all samples were clearly positive while a negative control, human normal thyroid cells, was negative). Enzyme assays showed that the cells which were tested at passage 6 (P6) secreted 1820 IU/ml amylase activity into the medium. Amylase is a characteristic marker for parotid gland secretion. On the basis of the findings of these three major salivary proteins, the cultures were found to be well differentiated human parotid gland cells that would be suitable for grafting.

The contents of each of the references cited in the present application, including publications, patents, and patent applications, are herein incorporated by reference in their entirety.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing an expanded, enriched, non-transformed cell culture of mammalian pancreatic endocrine cells, comprising the steps of:

(a) selecting said pancreatic endocrine cells from pancreatic tissue;

(b) concentrating said selected cells;

(c) resuspending said concentrated cells in a culture medium;

(d) culturing said resuspended cells for a time and under conditions to effect sustained cell division; and (e) passaging said cultured cells periodically to expand said culture;

wherein said culture medium is Coon's 4506.035 or Coon's 4506.07, and said culture is substantially free of fibroblast, macrophage, and capillary endothelial cells.

2. The method of claim 1, wherein said cell culture has undergone at least seven population doublings.

3. The method of claim 1, wherein said pancreatic endocrine cells are selected from the group consisting of alpha cells, beta cells, delta cells, pluripotent cells, and mixtures thereof.

4. The method of claim 3, wherein said pancreatic endocrine cells comprise at least two different types of pancreatic endocrine cells selected from the group consisting of alpha cells, beta cells, and delta cells.

5. The method of claim 1, wherein said pancreatic endocrine cells comprise human pancreatic endocrine cells.

6. The method of claim 5, wherein said cell culture has undergone at least seven population doublings.

7. A method for preparing clonal strains of an expanded non-transformed cell culture of mammalian pancreatic endocrine cells, comprising the steps of:

(a) culturing the cell culture obtained according to the method of claim 1;

(b) growing said culture to confluence;

(c) dissociating said cells;

(d) inoculating said disassociated cells into a culture vessel that contains a pancreatic endocrine cell conditioned Coon's 4506.035 or Coon's 4506.07 medium for a first plating and culturing said inoculated cells to produce colonies of cells;

(e) harvesting individual colonies of cells;

(f) inoculating said colonies into a culture vessel for a second plating and culturing said inoculated cells; and (g) passaging the cells of step (f) periodically.

8. The method of claim 7, wherein said cell culture has undergone at least seven population doublings.

9. The method of claim 7, wherein said pancreatic tissue is human.

10. The method of claim 9, wherein said pancreatic endocrine cells are selected from the group consisting of alpha cells, beta cells, delta cells, pluripotent cells, and mixtures thereof.

11. The method of claim 10, wherein said pancreatic endocrine cells comprise at least two different types of pancreatic endocrine cells selected from the group consisting of alpha cells, beta cells and delta cells.

12. The method of claim 11, wherein said cells are matrix-embedded.

13. A method for producing an expanded, non-transformed cell culture of mammalian thyroid or parathyroid cells, comprising the steps of:

(a) selecting said thyroid or parathyroid cells from thyroid or parathyroid tissue;

(b) concentrating said selected cells;

(c) resuspending said concentrated cells in a culture medium;

(d) culturing said resuspended cells for a time and under conditions to effect sustained cell division; and (e) passaging said cultured cells periodically to expand culture;

wherein said culture medium is Coon's 4506.035 or Coon's 4506.07, modified so that the concentration of $MgCl_2$ is about 0.48 mM, the concentration of hydrocortisone is 3.5 ng/ml, the concentration of selenous acid is about 2 ng/ml, the triiodothyronine concentration is about 3 pg/ml, the final concentration of bovine hypothalamus extract is about 75 µg protein/ml, and the final concentration of bovine pituitary extract is about 5 µg protein/ml, and said culture is substantially free of fibroblast, macrophage, and capillary endothelial cells.

14. The method of claim 13, wherein said cell culture has undergone at least seven population doublings.

15. A method for preparing clonal strains of an expanded, non-transformed cell culture of mammalian thyroid or parathyroid cells, comprising the steps of:

(a) culturing the cell culture obtained according to the method of claim 13;

(b) growing said culture to confluence;

(c) dissociating said cells;

(d) inoculating said dissociated cells into a culture vessel that contains a thyroid or parathyroid cell conditioned Coon's 4506.035 or Coon's 4506.07 medium for a first plating and culturing said inoculated cells to produce colonies of cells;

(e) harvesting individual colonies of cells;

(f) inoculating said colonies of cells into a culture vessel for a second plating and culturing said inoculated cells; and (g) passaging the cultured cells of step (f) periodically.

16. The method of claim 15, wherein said mammalian thyroid or parathyroid cell is human thyroid or parathyroid cell.

* * * * *